United States Patent
Chin et al.

(10) Patent No.: US 9,913,668 B2
(45) Date of Patent: Mar. 13, 2018

(54) INTERSPINOUS FIXATION IMPLANT

(75) Inventors: Kingsley R. Chin, Wilton Manors, FL (US); Matthew Ibarra, Lakewood, CA (US); Craig Kingsbury Henshaw, Charlestown, MA (US); Michael Drnek, Boston, MA (US)

(73) Assignee: SPINEFRONTIER, INC, Malden, MA (US)

( * ) Notice: Subject to any disclaimer, the term of this patent is extended or adjusted under 35 U.S.C. 154(b) by 0 days.

(21) Appl. No.: 13/182,524

(22) Filed: Jul. 14, 2011

(65) Prior Publication Data
US 2012/0016418 A1 Jan. 19, 2012

Related U.S. Application Data

(60) Provisional application No. 61/364,497, filed on Jul. 15, 2010.

(51) Int. Cl.
*A61B 17/70* (2006.01)
*A61B 17/80* (2006.01)

(52) U.S. Cl.
CPC ...... *A61B 17/7068* (2013.01); *A61B 17/8052* (2013.01)

(58) Field of Classification Search
CPC ........ A61F 2/4405; A61F 2/44; A61F 2/4455; A61F 2002/4475; A61B 17/7047; A61B 17/70; A61B 17/7068; A61B 17/7062
USPC .......................... 606/248, 249, 290, 250–253
See application file for complete search history.

(56) References Cited

U.S. PATENT DOCUMENTS

| | | | |
|---|---|---|---|
| 5,645,599 A | 7/1997 | Samani | |
| 2002/0151899 A1* | 10/2002 | Bailey et al. | 606/69 |
| 2003/0040746 A1 | 2/2003 | Mitchell et al. | |
| 2003/0216736 A1 | 11/2003 | Robinson et al. | |
| 2006/0247640 A1 | 11/2006 | Blackwell et al. | |
| 2006/0293662 A1 | 12/2006 | Boyer et al. | |
| 2007/0162001 A1 | 7/2007 | Chin et al. | |
| 2007/0179500 A1 | 8/2007 | Chin et al. | |
| 2007/0233082 A1 | 10/2007 | Chin et al. | |
| 2008/0167655 A1 | 7/2008 | Wang | |
| 2008/0183211 A1* | 7/2008 | Lamborne et al. | 606/249 |
| 2010/0087860 A1 | 4/2010 | Chin et al. | |
| 2010/0087869 A1 | 4/2010 | Abdou | |

(Continued)

FOREIGN PATENT DOCUMENTS

| | | |
|---|---|---|
| EP | EP1418854 | 5/2003 |
| WO | WO2007070819 A2 | 6/2007 |
| WO | WO2010016949 A1 | 2/2010 |

(Continued)

*Primary Examiner* — Julianna N Harvey
(74) *Attorney, Agent, or Firm* — AKC Patents, LLC; Aliki K. Collins

(57) ABSTRACT

An implantable assembly for stabilization of two adjacent spinous processes in a spinal column includes an elongated first component extending along a first axis, an elongated second component extending along a second axis, a hub spacer, means for inserting and securing the hub spacer transversely through the interspinous ligament separating the first and second spinous processes and means for clamping and securing first and second spinous processes of first and second adjacent vertebras, respectively, between the first and second components. The first and second components are arranged opposite and parallel to each other and are separated by the hub spacer.

24 Claims, 27 Drawing Sheets

(56) References Cited

U.S. PATENT DOCUMENTS

2011/0022090 A1 1/2011 Gordon et al.
2011/0144692 A1 6/2011 Saladin et al.

FOREIGN PATENT DOCUMENTS

WO WO2010068829 A2 6/2010
WO WO2011031924 A2 3/2011

* cited by examiner

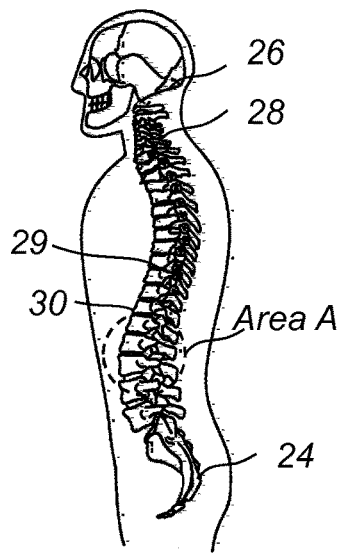
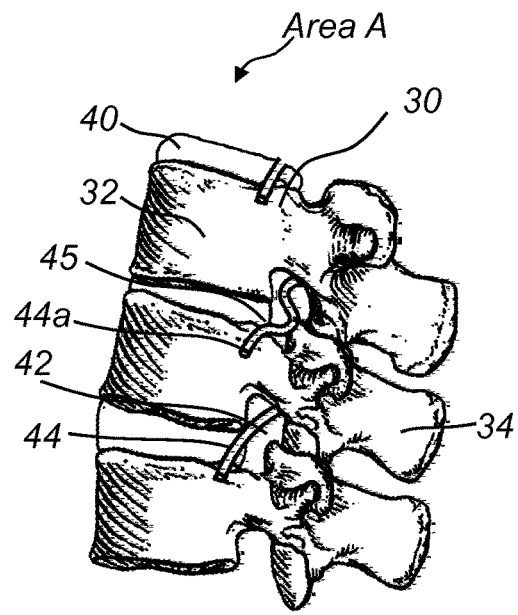
FIG. 1A  FIG. 1B
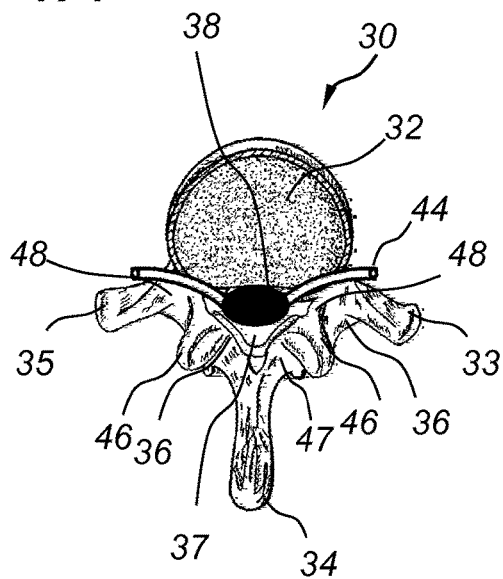
FIG. 1C

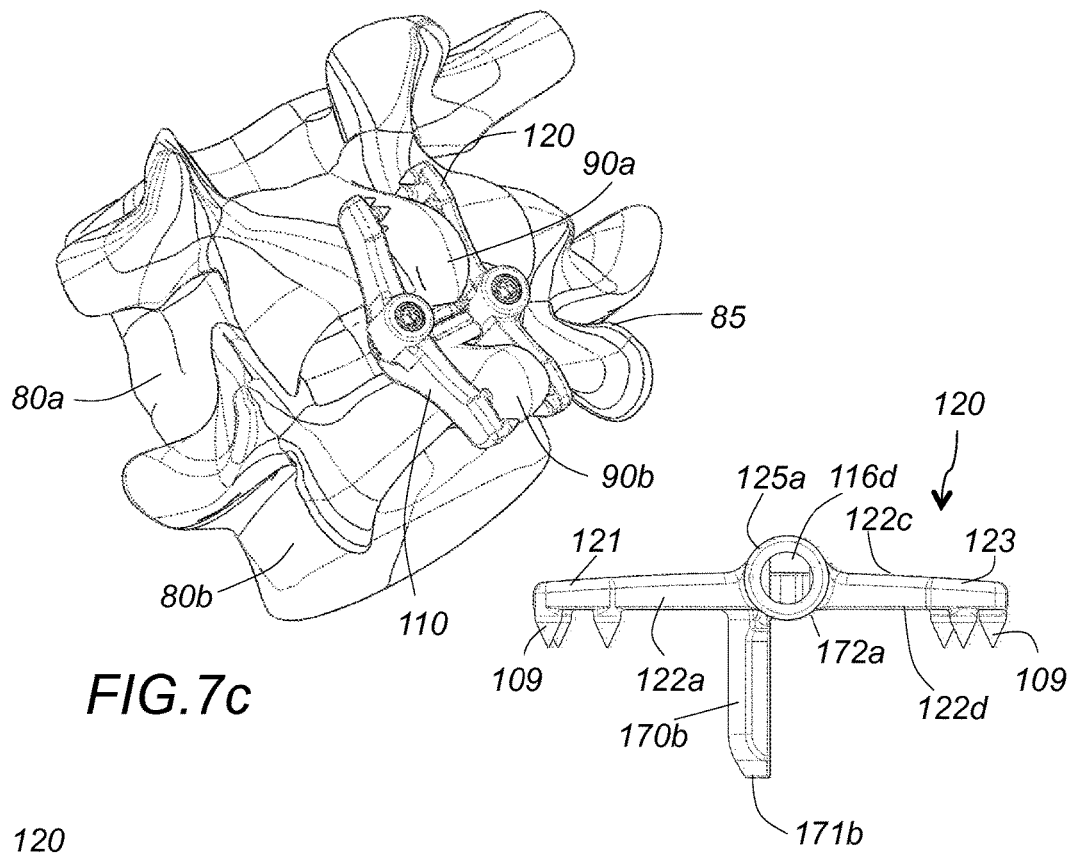
FIG.7c
FIG.7d
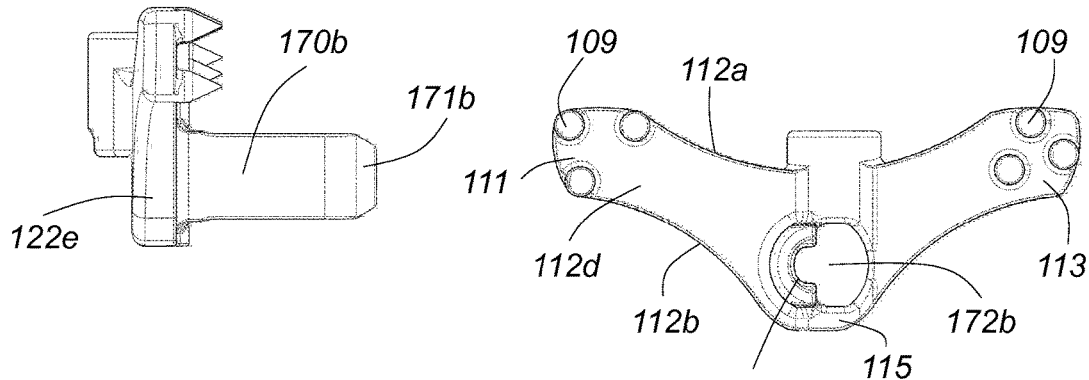
FIG.7e
FIG.7f

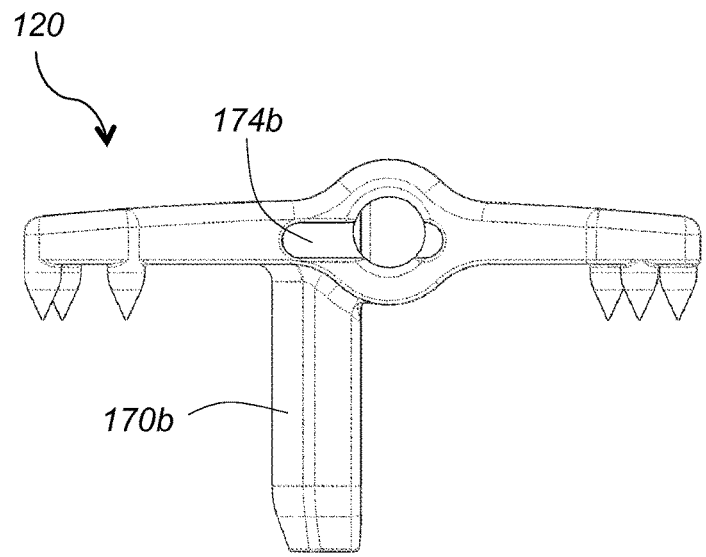
FIG.8c
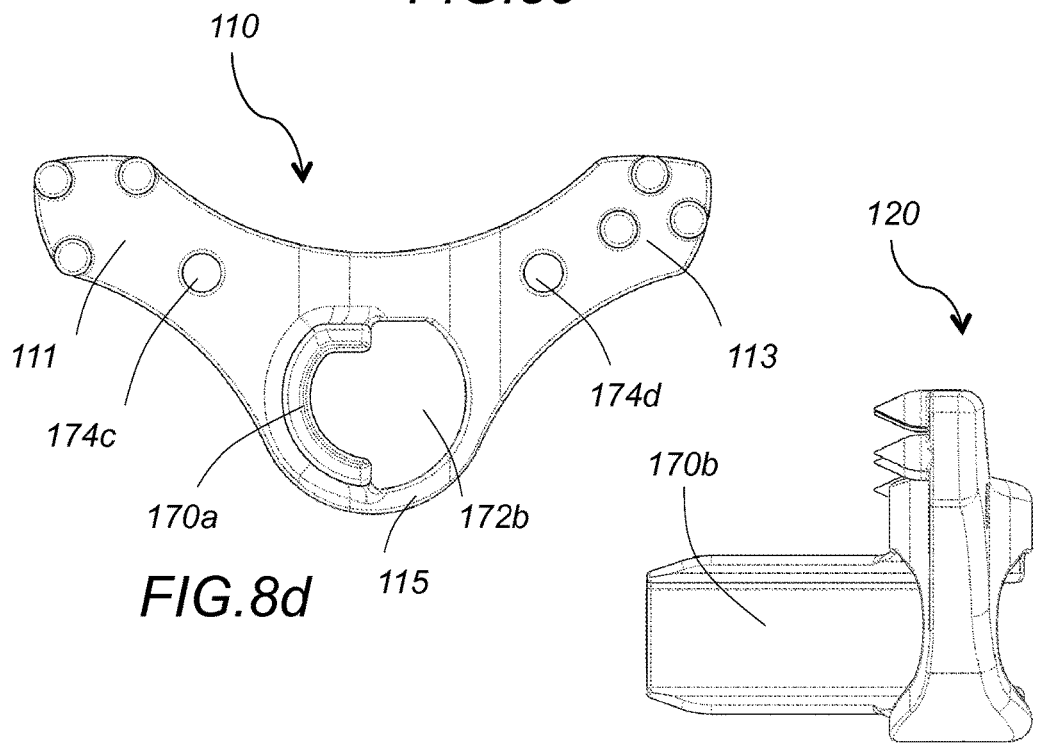
FIG.8d
FIG.8e

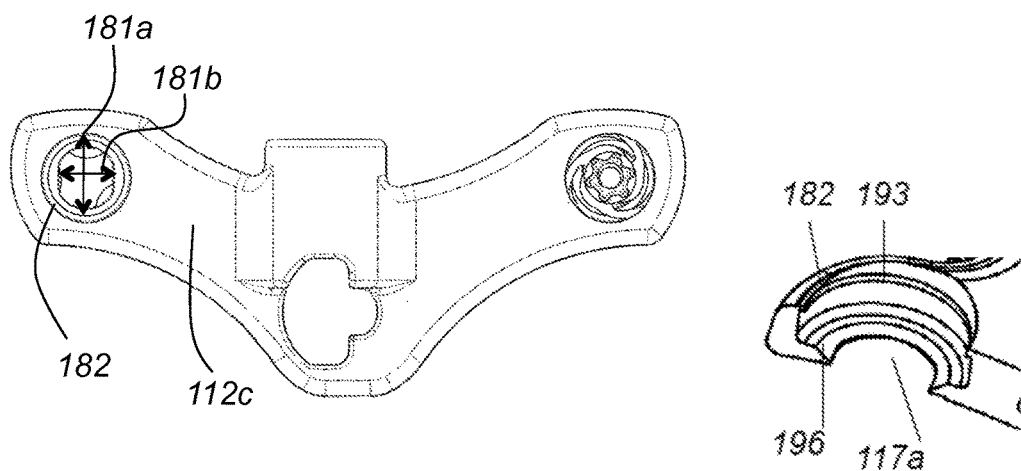
FIG.9d
FIG.9g
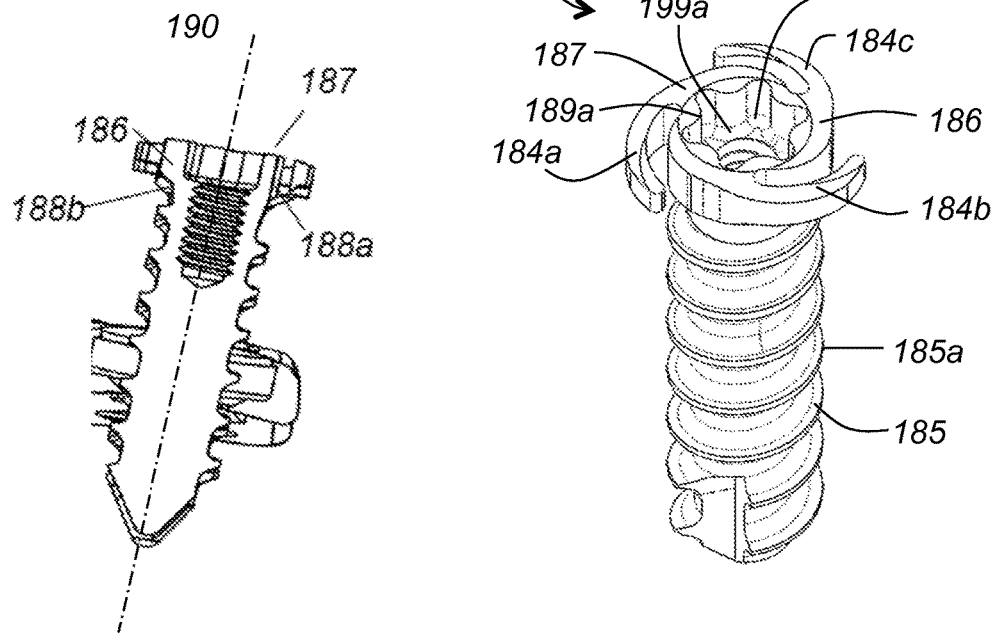
FIG.9f
FIG.9e

INTERSPINOUS FIXATION IMPLANT

CROSS REFERENCE TO RELATED CO-PENDING APPLICATIONS

This application claims the benefit of U.S. provisional application Ser. No. 61/364,497 filed Jul. 15, 2010 and entitled "INTERSPINOUS FIXATION IMPLANT", the contents of which are expressly incorporated herein by reference.

FIELD OF THE INVENTION

The present invention relates to a system and a method for spinal stabilization through an interspinous implant, and more particularly to spinal stabilization through attachment of an improved interspinous implant to the spinous processes along one or more vertebras.

BACKGROUND OF THE INVENTION

The human spine comprises individual vertebras 30 (segments) that are connected to each other to form a spinal column 29, shown in FIG. 1A. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relieve the patient of discomfort.

Several spinal fixation systems exist for stabilizing the spine so that bony fusion is achieved. The majority of these fixation systems utilize rods that attach to screws threaded into the vertebral bodies or the pedicles 48, shown in FIG. 1C. In some cases component fixation systems are also used to fuse two adjacent vertebral segments. The component fixation systems usually include two longitudinal components that are each placed laterally to connect two adjacent pedicles of the segments to be fused. The longitudinal components may be plates, rods, wires, among others. This system can be extended along the sides of the spine by connecting two adjacent pedicles at a time, similar to the concept of a bicycle chain. Current component fixation systems are basically designed to function in place of rods with the advantage of allowing intersegmental fixation without the need to contour a long rod across multiple segments. Both the component systems and the rod systems add bulk along the lateral aspect of the spine and limit access to the pars and transverse processes for decortication and placement of bone graft. In order to avoid this limitation many surgeons decorticate before placing the rods. However, decortication is not always desirable because it increases the amount of blood loss and makes it more difficult to maintain a clear operative field. Placing rods or components lateral to the spine leaves the center of the spinal canal that contains the dura, spinal cords and nerves completely exposed. In situations where problems develop at the junction above or below the fused segments additional fusion may be necessary. However, the rod fixation system is difficult to extend to higher or lower levels that need to be fused. Although there are connectors and techniques to lengthen the fixation via rods, they tend to be complex, difficult to use and time consuming.

Accordingly, there is a need for a spinal stabilization device that does not add bulk to the lateral aspect of the spine, is extendable and does not limit access to the pars and transverse processes for decortication and placement of bone graft.

SUMMARY OF THE INVENTION

In general, in one aspect, the invention features an implantable assembly for stabilization of two adjacent spinous processes in a spinal column. The implantable spinous process fixation assembly includes elongated first and second components that are arranged opposite and parallel to each other and are separated by a hub spacer. First and second spinous processes of first and second adjacent vertebras are clamped between the first and second components and are separated by the hub spacer that fits transversely through the interspinous ligament.

In general, in one aspect, the invention features an implantable assembly for stabilization of two adjacent spinous processes in a spinal column including an elongated first component extending along a first axis, an elongated second component extending along a second axis, a hub spacer, means for inserting and securing the hub spacer transversely through the interspinous ligament separating the first and second spinous processes and means for clamping and securing first and second spinous processes of first and second adjacent vertebras, respectively, between the first and second components. The first and second components are arranged opposite and parallel to each other and are separated by the hub spacer.

Implementations of this aspect of the invention may include one or more of the following features. The first component includes a first elongated body and a first integral post. The second component comprises a second elongated body and a second integral post. The first and second integral posts interface with each and form the hub spacer. Each of the first and second elongated bodies includes a parallelepiped structure having parallel front and back surfaces, parallel left and right surfaces and parallel top and bottom surfaces. The back surfaces of the first and second elongated bodies are convexly curved so that a middle portion of each of the first and second elongated bodies protrudes relative to the top and bottom portions of each of the first and second elongated bodies, respectively. The first elongated body further includes a first through-opening in the middle portion and the first through-opening extends from the left surface to the right surface and has a first cross section. The second elongated body further includes a first through-opening in the middle portion and the first through-opening extends from the left surface to the right surface and has a second cross section. The first integral post extends from the middle portion, perpendicularly to the right side surface of the first elongated body and comprises a hollow body. The hollow body is adjacent to the first through-opening and is oriented so that the hollow body's cross section matches the second cross of the first through-opening of the second elongated body. The second integral post extends from the middle portion, perpendicularly to the left side surface of the second elongated body and comprises a hollow body. The body is adjacent to the first through-opening and is oriented so that the body's cross section matches the first cross section of the first through-opening of the first elongated body. Each of the first and second elongated bodies further comprises a cylindrical projection extending from the middle portion perpendicular to the front surface and the cylindrical projection comprises a second through-opening extending from the front to the back surface of each of the first and second elongated bodies, and the second through-opening intersects the first through-opening perpendicularly. Each of the top portions of the first and second elongated bodies comprises one or more teeth protruding from the top right surface of the first elongated body and the top left surface of the second elongated body, respectively, and each of the bottom portions of the first and second elongated bodies comprises one or more teeth protruding from the bottom right surface of the first elongated body and the bottom left surface of the second elongated body, respectively. The first and second integral posts comprise rectangular cross-sections and are dimensioned to fit within the first through-openings in the second and first elongated bodies, respectively, and are oriented so as to interface with each other and to form a hollow parallelepiped hub spacer. The first and second integral posts comprise semi-circular cross-sections and are dimensioned to fit within the first through-openings in the second and first elongated bodies, respectively, and are oriented so as to interface with each other and to form a hollow cylindrical hub spacer. The assembly further includes first and second set-screws dimensioned to fit within the second through-openings of the first and second elongated bodies, respectively, and to secure the second and first integral posts within the first through-openings in the first and second elongated bodies, respectively. The first and second integral posts comprise tapered front ends or chamfered front ends. The means for inserting and securing the hub spacer transversely through the interspinous ligament separating the first and second spinous processes comprise the first and second through-openings, the tapered front ends and the first and second set-screws. The assembly further includes graft material placed within the hollow hub spacer. The first and second integral posts comprise side openings. The first and second elongated bodies further comprise first and second cutouts intersecting the second through-openings of the first and second elongated bodies, respectively, and wherein the cutouts are dimensioned to receive an inserter tool. The first elongated body further comprises third and fourth through-openings formed in the top and bottom portions of the first elongated body and the third and fourth through-openings extend from the left to the right surfaces of the first elongated body. The second elongated body further comprises third and fourth through-openings formed in the top and bottom portions of the second elongated body, and the third and fourth through-openings extend from the left to the right surfaces of the second elongated body. The assembly further includes first and second locking screws dimensioned to fit within and engage threads in the third and fourth through-openings, respectively. Each of the third and fourth through-openings of the first and second elongated bodies comprises a first diameter at the left surface of the first elongated body and at the right surface of the second elongated body, respectively, a second diameter at the right surface of the first elongated body and at the left surface of the second elongated body, respectively, and a third diameter in the area between the left and right surfaces of the corresponding elongated body and the first diameter is smaller than the third diameter, thereby forming a lip at the top of the through-openings and the third diameter is larger than the second diameter and the first diameter is larger than the second diameter, thereby forming a groove within the perimeter of the inner wall of the through-openings. Each of the first and second locking screws comprises a threaded main body and a head and the threaded main body comprises threads and the head comprises one or more flexible structures configured to be flexed and inserted into the groove and then unflex and remain captured within the groove. Each of the third and fourth through-openings comprises an oval-shaped perimeter and the oval-shaped perimeter comprises two parallel straight sides and two opposite curved sides and the distance between the two parallel straight sides is smaller than the major diameter of the threads of the first and second locking screws and the distance between the curved sides is equal to or larger than the major diameter of the threads of the first and second locking screws. The head of each of the first and second locking screws comprises a cylindrical main body and the one or more flexible structures comprise one or more flexible arms extending tangentially from the outer side surface of the cylindrical main body and curving counter-clockwise around the cylindrical main body and wherein the diameter of the head including the flexible arms in the unflexed position is larger than the first diameter of each of the third and fourth through openings and the flexible arms are configured to flex inward toward the outer side surface of the cylindrical main body when they come in contact with the lip while the locking screw is rotated clock-wise to be driven into the spinous processes and then the flexible arms unflex once they are below the lip. The head of each of the first and second locking screws comprises an opening extending into the threaded main body and the opening comprises an inner surface having six inward protruding lobes and a bottom having six grooves. The means for clamping and securing first and second spinous processes of first and second adjacent vertebras, respectively, between the first and second components, comprises at least one of the teeth or the first and second locking screws. Each of the first openings of the first and second elongated bodies further comprises a notch and each of the first and second integral posts comprises a groove configured to interface with the notch. At least one of the third and fourth openings comprises an axis not perpendicular to the first or second axis. The first and second components may have equal dimensions and shape.

In general, in one aspect, the invention features a method for stabilizing two adjacent spinous processes in a spinal column, including the following steps. First, providing an implantable stabilization assembly comprising an elongated first component extending along a first axis, an elongated second component extending along a second axis and a hub spacer. Next, arranging the first and second components opposite and parallel to each other and in contact with first and second spinous process of adjacent first and second vertebras, respectively, and separating them by the hub spacer. Next, inserting and securing the hub spacer transversely through the interspinous ligament separating the first and second spinous processes, and then clamping and securing the first and second spinous processes between the first and second components.

Among the advantages of this invention may be one or more of the following. The assembly stabilizes vertebras by attaching components to the spinous processes of the vertebras. This stabilization device does not add bulk to the lateral aspect of the spine and does not limit access to the pars and transverse processes for decortication and placement of bone graft. The compact form of the implant assembly allows it to be implanted via mini-open surgery. The device form conforms to the local vertebral anatomy. In particular, the adjustable plates and hub fit to the spinous process contour. The device may be used alone or as adjunct to facet or pedicle screw systems. It provides multi-level (i.e., multi-vertebra) fusion through replication of the basic unit. The device is securely attached to the spinous processes via the center post, individual components and pins. The fenestrated spacer enables application of graft material and promotes bone growth through the device.

The details of one or more embodiments of the invention are set forth in the accompanying drawings and description below. Other features, objects and advantages of the invention will be apparent from the following description of the preferred embodiments, the drawings and from the claims

BRIEF DESCRIPTION OF THE DRAWINGS

Referring to the figures, wherein like numerals represent like parts throughout the several views:

FIG. 1A is a side view of the human spinal column;

FIG. 1B is an enlarged view of area A of FIG. 1A;

FIG. 1C is an axial cross-sectional view of a lumbar vertebra;

FIG. 2c is a perspective view of the front of the first component of the interspinous fixation implant of FIG. 2a;

FIG. 2d is a perspective view of the front of the second component of the interspinous fixation implant of FIG. 2a;

FIG. 2e is a cross-sectional view along plane AA' of the interspinous fixation implant of FIG. 2a;

FIG. 3b is an exploded perspective view of the interspinous fixation implant of FIG. 3a;

FIG. 4b is a perspective view of the front of the second component of the interspinous fixation implant of FIG. 4a;

FIG. 4c is a perspective view of the back of the first component of the interspinous fixation implant of FIG. 4a;

FIG. 5b is a perspective view of the front of the second component of the interspinous fixation implant of FIG. 5a;

FIG. 5c is a perspective view of the back of the first component of the interspinous fixation implant of FIG. 5a;

FIG. 6b is an exploded view of the interspinous fixation implant of FIG. 6a;

FIG. 6c is a front view of the second component of the interspinous fixation implant of FIG. 6a;

FIG. 6d is a side view of the interspinous fixation implant of FIG. 6a;

FIG. 6e is a top view of the first component of the interspinous fixation implant of FIG. 6a;

FIG. 7b is an exploded view of the interspinous fixation implant of FIG. 7a;

FIG. 7c is a perspective view of the interspinous fixation implant of FIG. 7a securing two adjacent vertebras;

FIG. 7d is a front view of the second component of the interspinous fixation implant of FIG. 7a;

FIG. 7e is a top view of the first component of the interspinous fixation implant of FIG. 7a;

FIG. 7f is a cross-sectional view along plane A2-A2' of the interspinous fixation implant of FIG. 7a;

FIG. 8b is an exploded view of the interspinous fixation implant of FIG. 8a;

FIG. 8c is a front view of the second component of the interspinous fixation implant of FIG. 8a;

FIG. 8d is a side view of the interspinous fixation implant of FIG. 8a;

FIG. 8e is a top view of the second component of the interspinous fixation implant of FIG. 8a;

FIG. 8f is a perspective view of the back of the first component of the interspinous fixation implant of FIG. 8a;

FIG. 8g is a top view of the first component of the interspinous fixation implant of FIG. 8a;

FIG. 9b is a partially exploded view of the interspinous fixation implant of FIG. 9a;

FIG. 9c is an exploded view of the interspinous fixation implant of FIG. 9a;

FIG. 9d is a side view of the interspinous fixation implant of FIG. 9a;

FIG. 9e is a perspective view of the fastening screw 180a of FIG. 9c;

FIG. 9f is a cross-sectional view of fastening screw 180a of FIG. 9a;

FIG. 9g is a cross-sectional view of opening 117a of FIG. 9a;

FIG. 10b is an exploded view of the interspinous fixation implant of FIG. 10a;

DETAILED DESCRIPTION OF THE INVENTION

The present invention relates to a system and a method for improved spinous process fixation implants. Implantable spinous process fixation devices include elongated first and second components that are arranged opposite and parallel to each other and are separated by a hub spacer. First and second spinous processes of first and second adjacent vertebras are clamped between the first and second components and are separated by the hub spacer that fits transversely through the interspinous ligament.

Figure 2A:
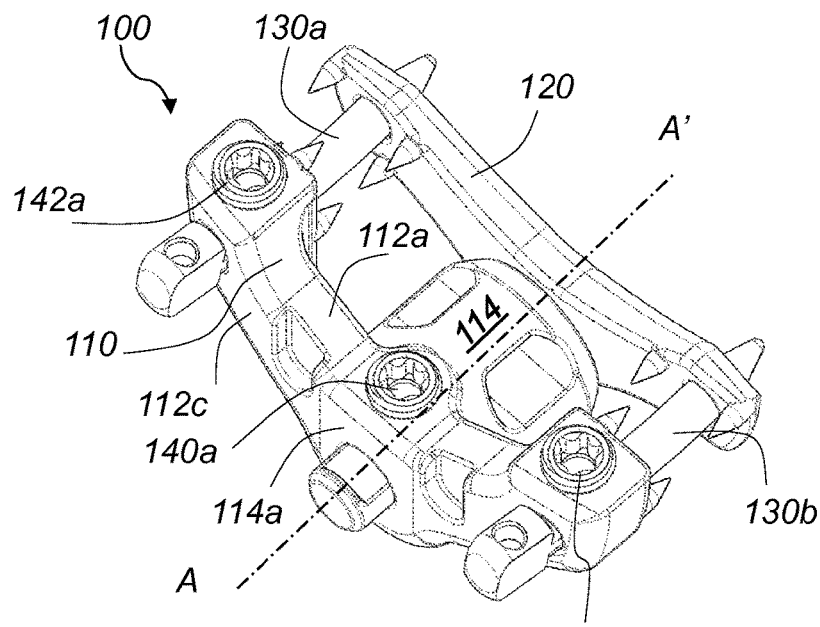
FIG. 2a is a perspective view of a first embodiment of the interspinous fixation implant according to this invention.
Figure 2B:
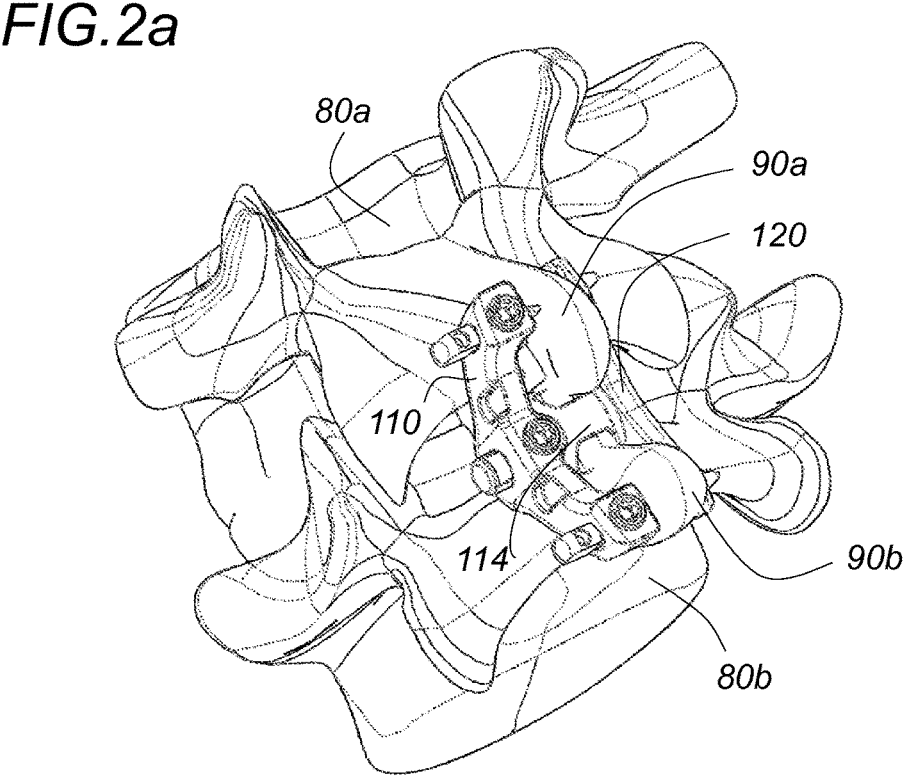
FIG. 2b is a perspective view of the interspinous fixation implant of FIG. 2a securing two adjacent vertebras.
Figure 2C:
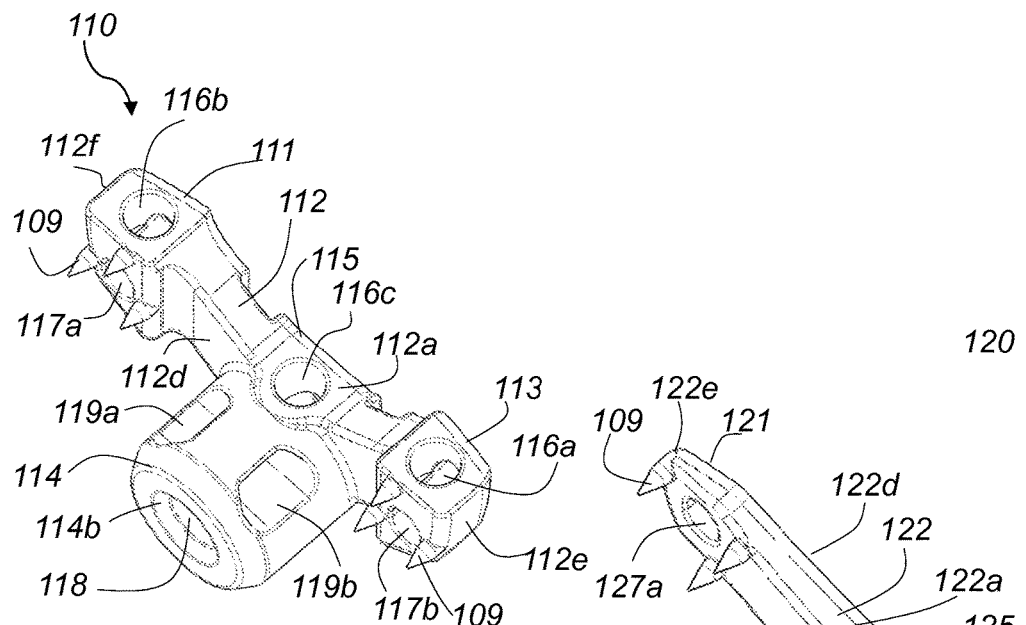

Referring to FIG. 2*a*-2*e*, spinous process fixation implant 100 includes first component 110, second component 120, top and bottom pins, 130*a*, 130*b* and set screws 140*a*, 142*a*, 142*b*. First component 110 includes an elongated body 112 and a cylindrical hub 114. Elongated body 112 has an essentially parallelepiped structure having parallel front and back surfaces 112*a*, 112*b*, parallel left and right side surfaces 112*c*, 112*d* and parallel top and bottom surfaces 112*e*, 112*f*, respectively. Elongated body 112 is convexly curved so that its top and bottom portions 111, 113 protrude forward relative to its middle portion 115. Top portion 111 includes first opening 116*a* extending from the front surface 112*a* to the back surface 112*b* and second opening 117*a* extending from the left surface 112*c* to the right surface 112*d*. Top portion 111 also includes teeth 109 protruding from the top of right surface 112*d*. Bottom portion 113 also includes first opening 116*b* extending from the front surface 112*a* to the back surface 112*b* and second opening 117*b* extending from the left surface 112*c* to the right surface 112*d*. Bottom portion 113 also includes teeth 109 protruding from the bottom of right surface 112*d*. Openings 117*a*, 117*b* have diameters slightly larger or equal to the diameters of top and bottom pins 130*a*, 130*b*, respectively, so that top and bottom pins 130*a*, 130*b* can pass through them. Openings 116*a*, 116*b* receive set screws 142*a*, 142*b* and have dimensions that match the dimensions of screws 142*a*, 142*b*. Screws 142*a*, 142*b* secure the positions of top and bottom pins 130*a*, 130*b* within openings 117*a*, 117*b*, respectively. Middle portion 115 includes a through-opening 116*c* extending from the front surface 112*a* to the back surface 112*b*. Opening 116*c* receives set screw 140*a* and has dimensions matching the dimensions of screw 140*a*. As will be described later, screw 140*a* secures the position of cylindrical post 124 of second component 120 within an opening 118 of cylindrical hub 114. Cylindrical hub 114 extends perpendicularly to the right side surface 112*d* of the elongated body 112 from its middle portion 115. Cylindrical hub 114 includes an opening 118 extending from its left side 114*a* to its right side 114*b*, as shown in FIG. 2*c*. As was mentioned above, opening 118 receives cylindrical post 124 of component 120 and has a diameter slightly larger or equal to the diameter of cylindrical post 124. Cylindrical hub 114 also includes openings 119*a*, 119*b* used for holding graft material used in fusing the spinous processes together. In one example, elongated body 112 has a length in the range of about 37-45 mm and width of about 2 mm and cylindrical hub 114 has a diameter of about 8-16 mm.

Figure 2D:
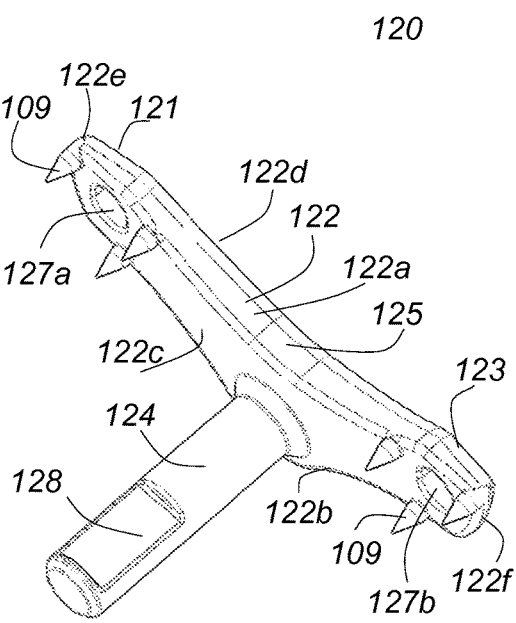
Figure 2E:
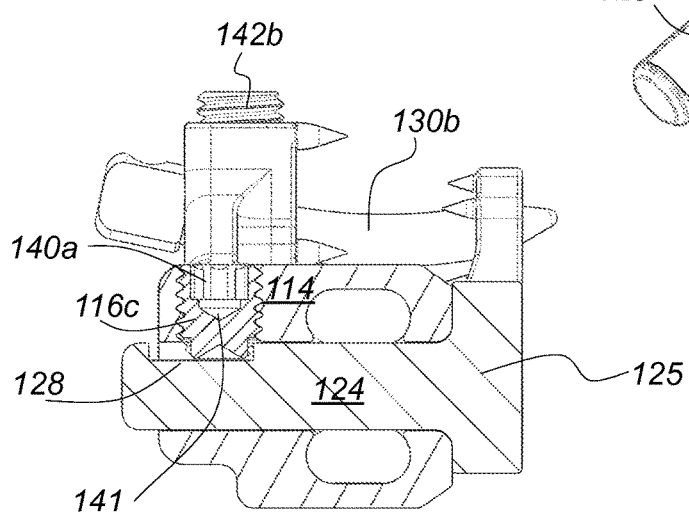

Referring to FIG. 2*d*, second component 120 includes an elongated body 122 and an integral cylindrical post 124. Elongated body 122 has an essentially parallelepiped structure having parallel front and back surfaces 122*a*, 122*b*, parallel left and right side surfaces 122*c*, 122*d* and parallel top and bottom surfaces 122*e*, 122*f*, respectively. Elongated body 122 is also convexly curved so that its top and bottom portions 121, 123 protrude forward relative to its middle portion 125. Top portion 121 includes opening 127*a* extending from the left surface 122*c* to the right surface 122*d*. Top portion 121 also includes teeth 109 protruding from the top of left surface 122*c*. Bottom portion 123 also includes opening 127*b* extending from the left surface 112*c* to the right surface 112*d*. Bottom portion 123 also includes teeth 109 protruding from the bottom of left surface 122*c*. Openings 127*a*, 127*b* have diameters slightly larger than the diameters of top and bottom pins 130*a*, 130*b*, respectively, so that top and bottom pins 130*a*, 130*b* can pass through them. Cylindrical post 124 extends perpendicularly to the left side surface 122*c* of the elongated body 122 from its middle portion 125. Cylindrical post 124 includes a flat cut out 128, as shown in FIG. 2*d*. As was mentioned above, opening 118 of cylindrical hub 114 receives cylindrical post 124 of component 120 and has a diameter slightly larger or equal to the diameter of cylindrical post 124. Screw 140*a* is screwed into opening 116*c* of elongated body 112 and secures the position of cylindrical post 124 within opening 118 of cylindrical hub 114. The end of the set-screw 141 has a ring shape that presses against the flat cut out 128 of the cylindrical post 124, as shown in FIG. 2*e*. In one example, elongated body 122 of has a length in the range of about 37-45 mm and width of about 2 mm and cylindrical hub 124 has a diameter of about 8-16 mm.

In operation first component 110 is placed in contact with the left sides of top and bottom spinous process 90*a*, 90*b* of adjacent vertebras 80*a*, 80*b*, respectively. Cylindrical hub 114 is placed in the space between the top and bottom spinous processes 90*a*, 90*b*, as shown in FIG. 2*b*. Hub 114 distracts the spinous processes 90*a*, 90*b* and prevents extension. Next, second component 120 is placed in contact with the right sides of top and bottom spinous process 90*a*, 90*b* of adjacent vertebras 80*a*, 80*b*, respectively, and cylindrical post 124 is inserted in the opening 118 of the cylindrical hub 114. Next, set screw 140*a* is screwed into opening 116*c* of the first component 110 to compress and secure the two components 110, 120 left and right of the top and bottom spinous processes 90*a*, 90*b*, respectively. Teeth 109 at the top and bottom portions of components 110, 120 penetrate into the sides of the top and bottom spinous processes 90*a*, 90*b*, respectively. Next, pins 130*a*, 130*b* are inserted into openings 117*a*, 117*b* of the first component 110, pass through previously formed openings in the spinous processes 90*a*, 90*b* and then through openings 127*a*, 127*b* of the second component 120. Finally, set screws 142*a*, 142*b* are screwed into openings 116a, 116b of the first component to secure the positions of pins 130a, 130b, respectively.

Figure 3A:
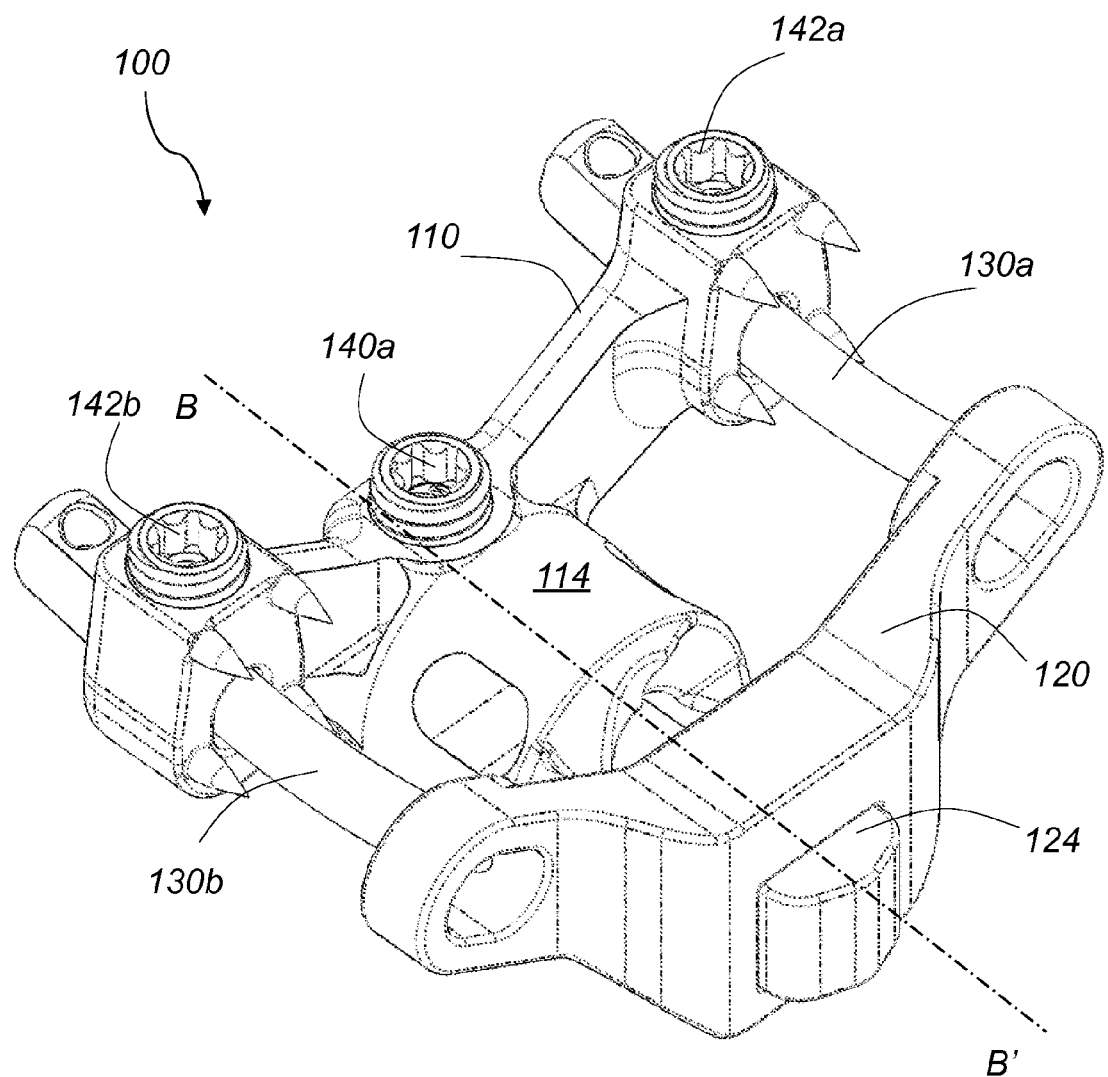
FIG. 3a is a perspective view of a second embodiment of the interspinous fixation implant according to this invention.
Figure 3B:
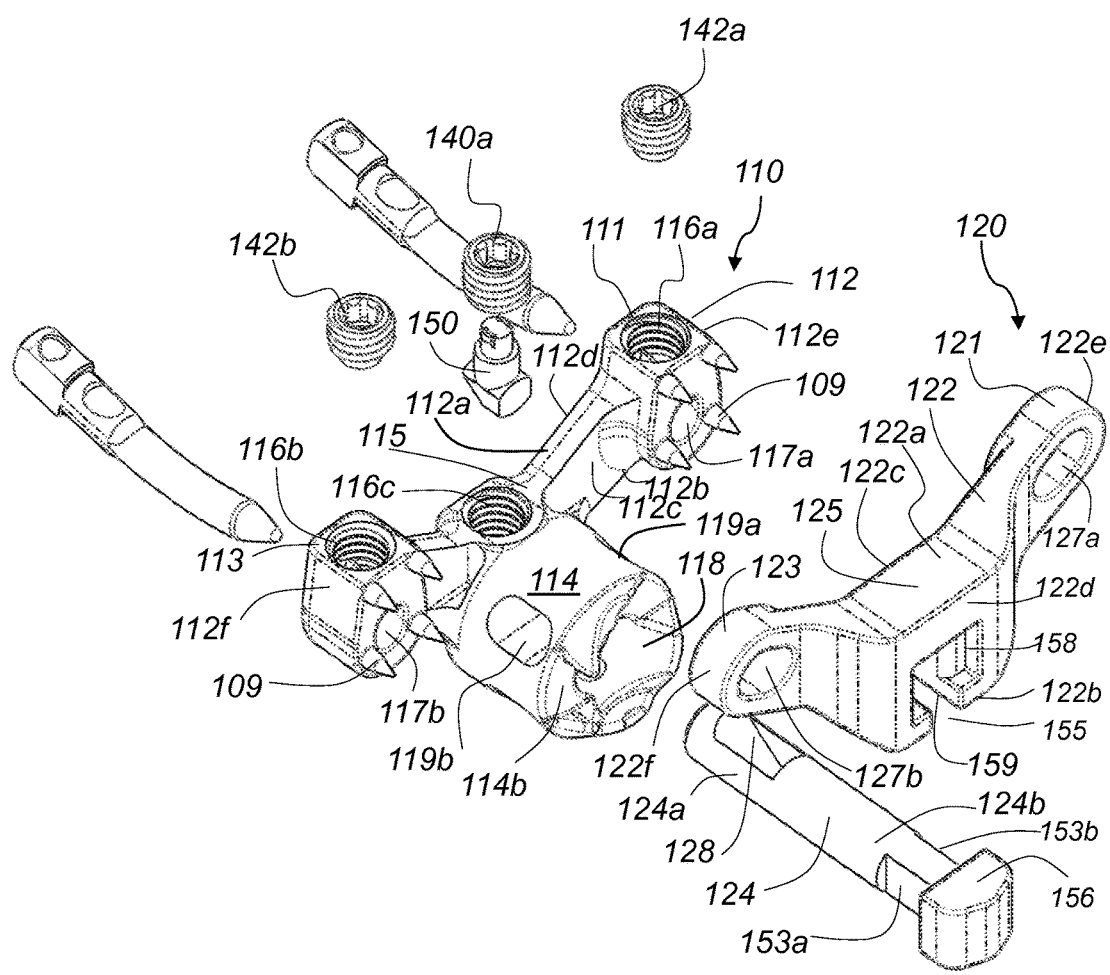
Figure 3C:
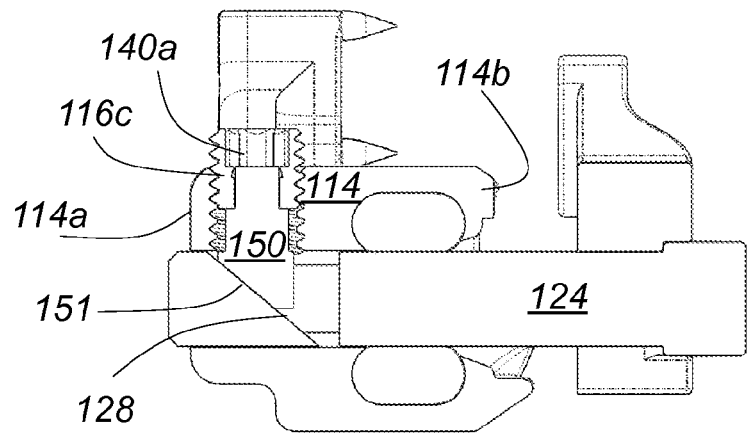
FIG. 3c is a cross-sectional view along plane BB' of the interspinous fixation implant of FIG. 3a with the wedge in the up position.

Referring to FIG. 3a-3d, spinous process fixation implant 100 includes first component 110, second component 120, cylindrical post 124, wedge/ramp 150, top and bottom pins, 130a, 130b and set screws 140a, 142a, 142b. First component 110 includes an elongated body 112 and a cylindrical hub 114. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115. Top portion 111 includes first opening 116a extending from the front surface 112a to the back surface 112b and second opening 117a extending from the left surface 112c to the right surface 112d. Top portion 111 also includes teeth 109 protruding from the top of right surface 112d. Bottom portion 113 also includes first opening 116b extending from the front surface 112a to the back surface 112b and second opening 117b extending from the left surface 112c to the right surface 112d. Bottom portion 113 also includes teeth 109 protruding from the bottom of right surface 112d. Openings 117a, 117b have diameters slightly larger or equal to the diameters of top and bottom pins 130a, 130b, respectively, so that top and bottom pins 130a, 130b can pass through them. Openings 116a, 116b receive set screws 142a, 142b and have dimensions that match the dimensions of screws 142a, 142b. Screws 142a, 142b secure the positions of top and bottom pins 130a, 130b within openings 117a, 117b, respectively. Middle portion 115 also includes opening 116c extending from the front surface 112a to the back surface 112b. Opening 116c receives set screw 140a and has dimensions matching the dimensions of screw 140a. As will be described later, set screw 140a secures the position of wedge/ramp 150 onto cylindrical post 124 after it is placed within an opening 118 of cylindrical hub 114. Cylindrical hub 114 extends perpendicularly to the left side surface 112d of the elongated body 112 from its middle portion 115. Cylindrical hub 114 includes an opening 118 extending from its left side 114a to its right side 114b, as shown in FIG. 3c. As was mentioned above, opening 118 receives cylindrical post 124 and has a diameter slightly larger or equal to the diameter of cylindrical post 124. Cylindrical hub 114 also includes openings 119a, 119b used for holding graft material used in fusing the spinous processes together.

Figure 3D:
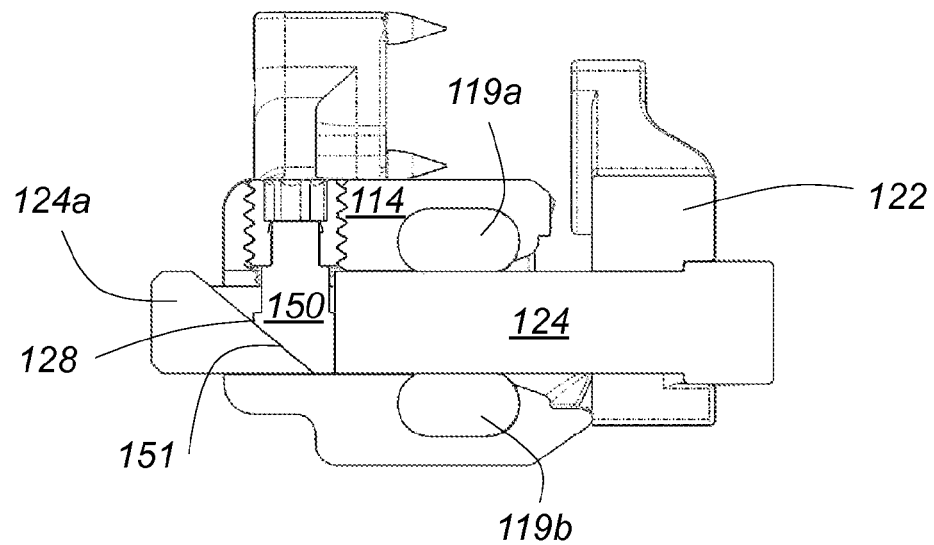
FIG. 3d is a cross-sectional view along plane BB' of the interspinous fixation implant of FIG. 3a with the wedge in the down position.

Referring to FIG. 3b, second component 120 includes an elongated body 122. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Top portion 121 includes opening 127a extending from the left surface 122c to the right surface 122d. Bottom portion 123 also includes opening 127b extending from the left surface 112c to the right surface 112d. Openings 127a, 127b have diameters slightly larger or equal to the diameters of top and bottom pins 130a, 130b, respectively, so that top and bottom pins 130a, 130b can pass through them. Middle portion 125 includes a through opening 155 extending from left side 122c to right side 122d. Opening 155 has essentially a cylindrical cross-section dimensioned for receiving cylindrical post 124. The cross-sectional geometry of opening 155 changes near the side surface 122d. In the example of FIG. 3b, opening 155 has a square cross-section in the area 158 near the side surface 122d. Square cut out 158 is dimensioned to receive block 156 of post 124, as will be described below. In this embodiment, post 124 is not integral with second component 120. Post 124 is essentially a cylindrical rod and includes an inclined cut out 128 at a first end 124a, square cut outs 153a, 153b at opposite end 124b and a block 156 attached to end 124b, as shown in FIG. 3b. As was mentioned above, opening 118 of cylindrical hub 114 receives cylindrical post 124 and has a diameter slightly larger or equal to the diameter of cylindrical post 124. Block 156 has a shape that matches the shape of the square cut out 158 of opening 155 and is dimensioned to fit within the square cut out 158. Opposite cut outs 153a, 153b also match corresponding side cut outs 159 within opening 155 and serve to set and indicate the orientation of the inclined cut out 128 at the opposite end 124a of the post 124. After post 124 is inserted into opening 155 and its position is oriented so that the inclined cut out is oriented facing up, wedge/ramp 150 is inserted into opening 116c and then screw 140a is screwed into opening 116c to secure the position of post 124 within opening 118 of cylindrical hub 114. Screw 140a moves into opening 116c and presses the wedge surface 151 of wedge/ramp 150 against the inclined cut out 128 of the cylindrical post 124, as shown in FIG. 3c and FIG. 3d.

In operation first component 110 is placed in contact with the left sides of top and bottom spinous process 90a, 90b of adjacent vertebras 80a, 80b, respectively. Cylindrical hub 114 is placed in the space between the top and bottom spinous processes 90a, 90b, as shown in FIG. 2b. Next, second component 120 is placed in contact with the right sides of top and bottom spinous process 90a, 90b of adjacent vertebras 80a, 80b, respectively, and then cylindrical post 124 is inserted in opening 155 of second component 120 and in opening 118 of the cylindrical hub 114. Post 124 is rotated and oriented so that block 156 sits within the cut out 158, thereby locking the position of post 124 relative to second component 120 and indicating that the inclined cutout 128 is oriented upwards, as was described above. In other embodiments, post 124 is inserted into opening 118 of component 110 prior to inserting and attaching component 110 in contact with the left sides of top and bottom spinous process 90a, 90b of adjacent vertebras 80a, 80b, respectively. Next, second component 120 is placed over rod 124 so that 156 sits within the cut out 158, and then is placed in contact with the right sides of top and bottom spinous process 90a, 90b of adjacent vertebras 80a, 80b, respectively. Next, wedge/ramp 150 is inserted into opening 116c of the first component 110 and then set screw 140a is screwed into opening 116c to press the wedge surface 151 of wedge/ramp 150 against the inclined cut out 128 of the cylindrical post 124. In this way wedge/ramp 150 compresses and secures component 110 onto post 124, and locks components 110, 120, left and right of the top and bottom spinous processes 90a, 90b, respectively. Teeth 109 at the top and bottom portions of component 110 penetrate into the left side of the top and bottom spinous processes 90a, 90b, respectively. Next, pins 130a, 130b are inserted into openings 117a, 117b of the first component 110, pass through previously formed openings in the spinous processes 90a, 90b and then through openings 127a, 127b of the second component 120. Finally, set screws 142a, 142b are screwed into openings 116a, 116b of the first component to secure the positions of pins 130a, 130b, respectively.

Figure 4A:
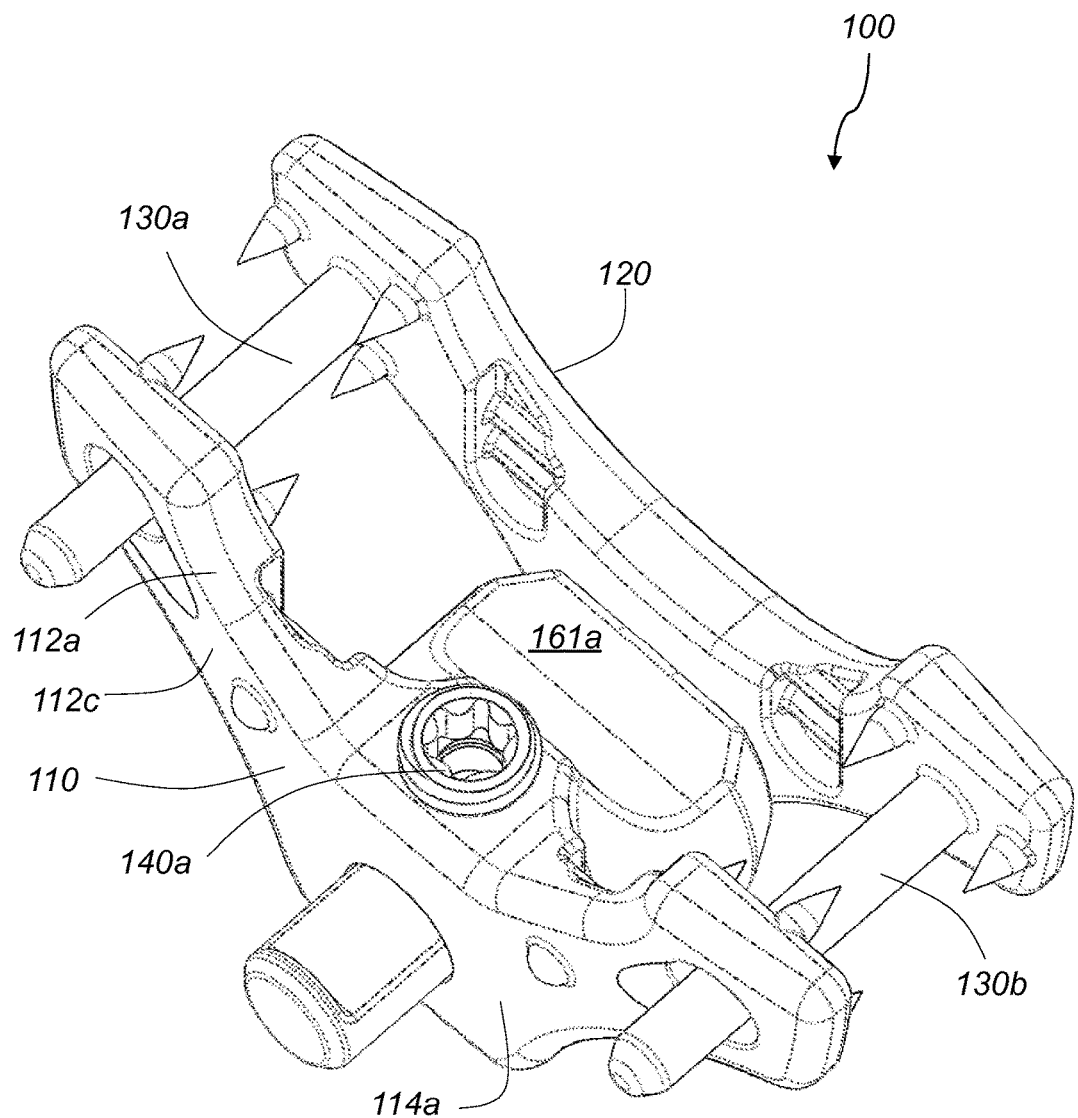
FIG. 4a is a perspective view of a third embodiment of the interspinous fixation implant according to this invention.
Figure 4B:
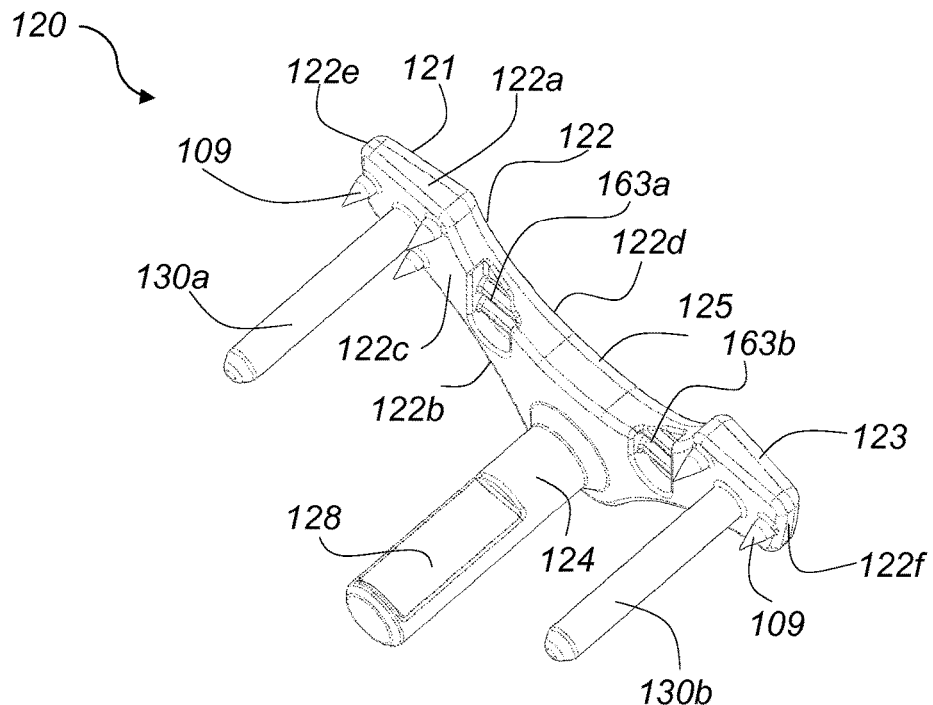
Figure 4C:
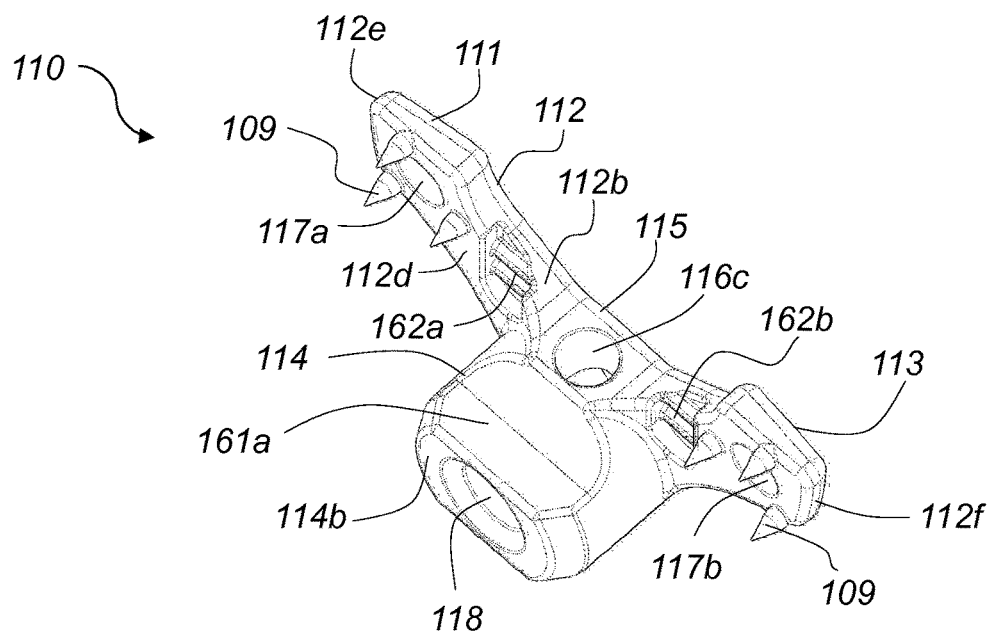

Referring to FIG. 4a-4c, spinous process fixation implant 100 includes first component 110, second component 120, and set screw 140a. First component 110 includes an elongated body 112 and a cylindrical hub 114. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115. Top portion 111 includes opening 117a extending from the left surface 112c to the right surface 112d. Top portion 111 also includes teeth 109 protruding from the top of right surface 112d. Bottom portion 113 also includes opening 117b extending from the left surface 112c to the right surface 112d. Bottom portion 113 also includes teeth 109 protruding from the bottom of right surface 112d. Openings 117a, 117b have diameters slightly larger or equal to the diameters of top and bottom pins 130a, 130b, respectively, so that top and bottom pins 130a, 130b can pass through them. Top and bottom pins 130a, 130b are integral with second component 120, as will be described below. Middle portion 115 also includes opening 116c extending from the front surface 112a to the back surface 112b. Opening 116c receives set screw 140a and has dimensions matching the dimensions of screw 140a. As will be described later, screw 140a secures the position of cylindrical post 124 of second component 120 within an opening 118 of cylindrical hub 114. Cylindrical hub 114 extends perpendicularly to the right side surface 112d of the elongated body 112 from its middle portion 115. Cylindrical hub 114 includes an opening 118 extending from its left side 114a to its right side 114b, as shown in FIG. 4c. As was mentioned above, opening 118 receives cylindrical post 124 of component 120 and has a diameter slightly larger or equal to the diameter of cylindrical post 124. Cylindrical hub 114 also includes straight cut out 161a extending from the front to back surfaces of hub 114 and used for holding graft material used in fusing the spinous processes together. Elongated body 112 also includes cut outs 162a, 162b used for holding the implant via an inserter tool (not shown).

Referring to FIG. 4b, second component 120 includes an elongated body 122 having an integral cylindrical post 124 and integral top and bottom pins, 130a, 130b. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Top portion 121 includes integral top pin 130a extending perpendicular to and from the top left surface 122c. Top portion 121 also includes teeth 109 protruding from the top of left surface 122c. Bottom portion 123 also includes bottom pin 130b extending perpendicular to and from the left surface 112c. Bottom portion 123 also includes teeth 109 protruding from the bottom of left surface 122c. Cylindrical post 124 extends perpendicularly to the left side surface 112c of the elongated body 122 from its middle portion 125. Cylindrical post 124 includes a flat cut out 128. As was mentioned above, opening 118 of cylindrical hub 114 receives cylindrical post 124 of component 120 and has a diameter slightly larger or equal to the diameter of cylindrical post 124. Screw 140a is screwed into opening 116c of elongated body 112 and secures the position of cylindrical post 124 within opening 118 of cylindrical hub 114. The end of the set-screw 141 has a ring shape that presses against the flat cut out 128 of the cylindrical post 124, as shown in FIG. 2e. Elongated body 122 also includes cut outs 163a, 163b used for holding the implant with an inserter tool (not shown).

In operation first component 110 is placed in contact with the left sides of top and bottom spinous process 90a, 90b of adjacent vertebras 80a, 80b, respectively. Cylindrical hub 114 is placed in the space between the top and bottom spinous processes 90a, 90b, as shown in FIG. 2b. Next, second component 120 is placed in contact with the right sides of top and bottom spinous process 90a, 90b of adjacent vertebras 80a, 80b, respectively, cylindrical post 124 is inserted in the opening 118 of the cylindrical hub 114 and top and bottom pins 130a, 130b are inserted through previously formed openings in the spinous processes 90a, 90b and then into openings 117a, 117b, of the first component 110, respectively. Next, set screw 140a is screwed into opening 116c of the first component 110 to compress and secure the two components 110, 120 left and right of the top and bottom spinous processes 90a, 90b, respectively. Teeth 109 at the top and bottom portions of components 110, 120 penetrate into the sides of the top and bottom spinous processes 90a, 90b, respectively.

Figure 5A:
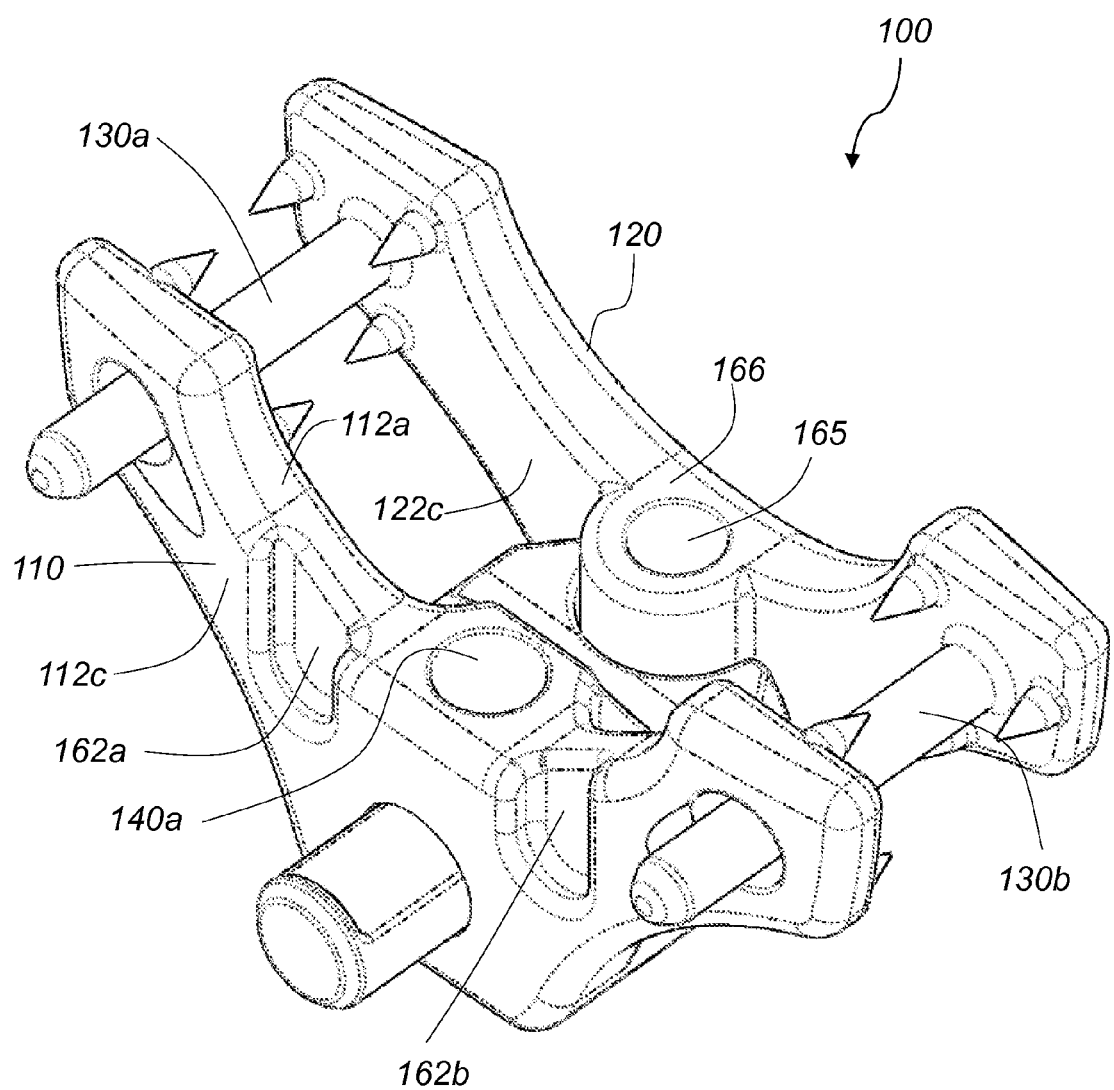
FIG. 5a is a perspective view of a fourth embodiment of the interspinous fixation implant according to this invention.
Figure 5B:
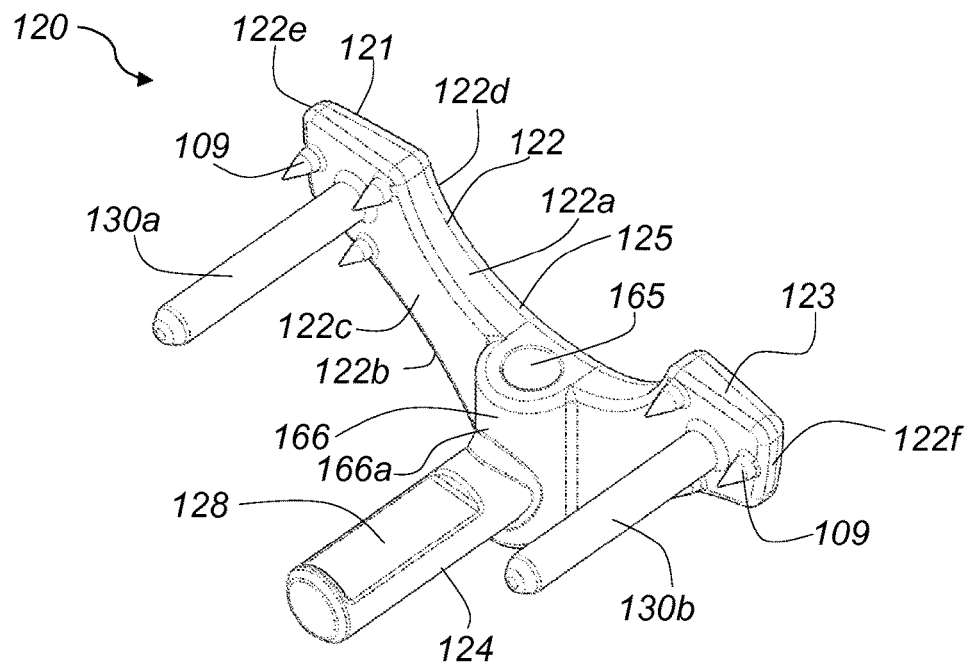
Figure 5C:
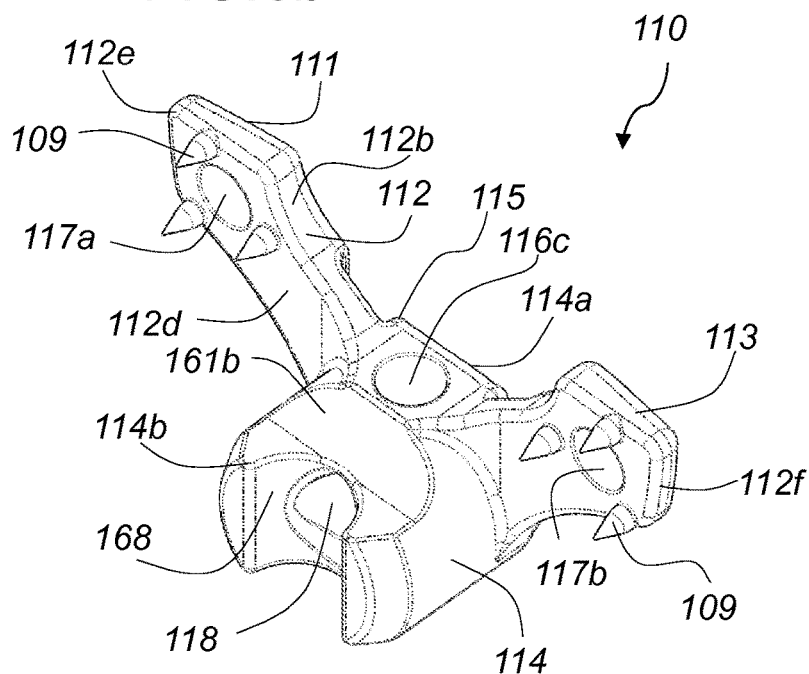

Referring to FIG. 5a-5c, spinous process fixation implant 100 includes first component 110, second component 120, and set screw 140a. First component 110 includes an elongated body 112 and a cylindrical hub 114. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115. Top portion 111 includes opening 117a extending from the left surface 112c to the right surface 112d. Top portion 111 also includes teeth 109 protruding from the top of right surface 112d. Bottom portion 113 also includes opening 117b extending from the left surface 112c to the right surface 112d. Bottom portion 113 also includes teeth 109 protruding from the bottom of right surface 112d. Openings 117a, 117b have diameters slightly larger or equal to the diameters of top and bottom pins 130a, 130b, respectively, so that top and bottom pins 130a, 130b can pass through them. Top and bottom pins 130a, 130b are integral with second component 120, as will be described below. Middle portion 115 also includes opening 116c extending from the front surface 112a to the back surface 112b. Opening 116c receives set screw 140a and has dimensions matching the dimensions of screw 140a. As will be described later, screw 140a secures the position of cylindrical post 124 of second component 120 within an opening 118 of cylindrical hub 114. Cylindrical hub 114 extends perpendicularly to the right side surface 112d of the elongated body 112 from its middle portion 115. Cylindrical hub 114 includes an opening 118 extending from its left side 114a to its right side 114b, as shown in FIG. 5c. As was mentioned above, opening 118 receives cylindrical post 124 of component 120 and has a diameter slightly larger or equal to the diameter of cylindrical post 124. Cylindrical hub 114 also includes straight cut outs 161a, 161b formed on top and bottom surfaces of hub 114. Cut outs 161a, 161b are used for holding graft material used in fusing the spinous processes together. Elongated body 112 also includes cut outs 162a, 162b used as gripping features for the inserter tool to grab onto. In this embodiment, hub 114 includes a cylindrical cut out 168 on its right side 114b. Cut out 168 is shaped and dimensioned to accommodate an integral cylindrical projection 166 formed on the left side 122c of the second component 120.

Referring to FIG. 5b, second component 120 includes an elongated body 122, an integral cylindrical post 124, integral cylindrical projection 166 and integral top and bottom pins,

130a, 130b. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Top portion 121 includes integral top pin 130a extending perpendicular to and from the top left surface 122c. Top portion 121 also includes teeth 109 protruding from the top of left surface 122c. Bottom portion 123 also includes bottom pin 130b extending perpendicular to and from the left surface 112c. Bottom portion 123 also includes teeth 109 protruding from the bottom of left surface 122c. Cylindrical projection 166 extends form the middle portion 125 and includes a threaded through opening 165 extending from the front surface 122a to the back surface 122b, as shown in FIG. 5b. Cylindrical projection 166 creates a cylinder key that fits into the cylindrical cut out 168 of the hub 114 of the first component 110, as shown in FIG. 5a. The inter-fitting of cylindrical projection 166 into cylindrical cut out 168 of the hub 114 creates a lock that prevents rotation of components 110, 120. The threaded opening 165 is used for inserting a threaded inserter tool (not shown). Cylindrical post 124 extends from the side surface 166a of the cylindrical projection 166 and is oriented perpendicularly to the left side surface 112c of the elongated body 122. Cylindrical post 124 includes a flat cut out 128, as shown in FIG. 5b. As was mentioned above, opening 118 of cylindrical hub 114 receives cylindrical post 124 of component 120 and has a diameter slightly larger or equal to the diameter of cylindrical post 124. Screw 140a is screwed into opening 116c of elongated body 112 and secures the position of cylindrical post 124 within opening 118 of cylindrical hub 114. The tip 141 of screw 140a moves into opening 116c and presses against the flat cut out 128 of the cylindrical post 124, as shown in FIG. 2e.

In operation first component 110 is placed in contact with the left sides of top and bottom spinous process 90a, 90b of adjacent vertebras 80a, 80b, respectively. Cylindrical hub 114 is placed in the space between the top and bottom spinous processes 90a, 90b, as shown in FIG. 2b. Next, second component 120 is placed in contact with the right sides of top and bottom spinous process 90a, 90b of adjacent vertebras 80a, 80b, respectively, cylindrical post 124 is inserted in the opening 118 of the cylindrical hub 114 and top and bottom pins 130a, 130b are inserted through previously formed openings in the spinous processes 90a, 90b and then into openings 117a, 117b, of the first component 110, respectively. Next, set screw 140a is screwed into opening 116c of the first component 110 to compress and secure the two components 110, 120 left and right of the top and bottom spinous processes 90a, 90b, respectively. Teeth 109 at the top and bottom portions of components 110, 120 penetrate into the sides of the top and bottom spinous processes 90a, 90b, respectively. Full insertion of cylindrical post 124 in opening 118 of the cylindrical hub 114 causes the inter-fitting of the cylindrical projection 166 with the cylindrical cut out 168 of the hub 114 and thereby prevents the rotation of the second component 120 relative to the first component 110.

Figure 6A:
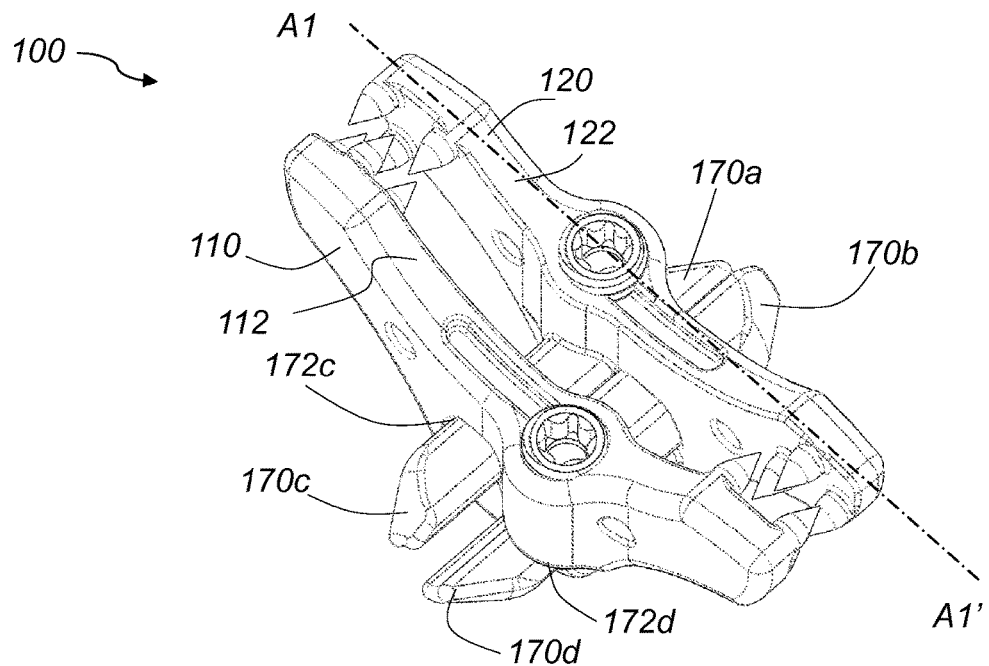
FIG. 6a is a perspective view of a fifth embodiment of the interspinous fixation implant according to this invention.
Figure 6B:
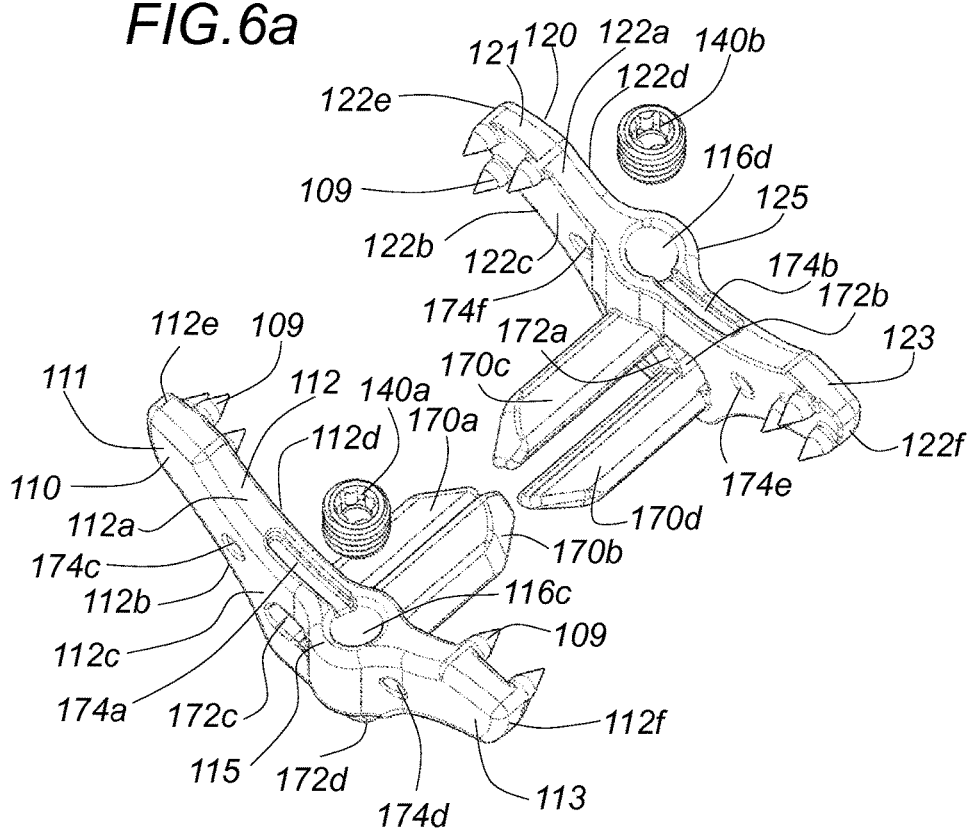
Figure 6C:
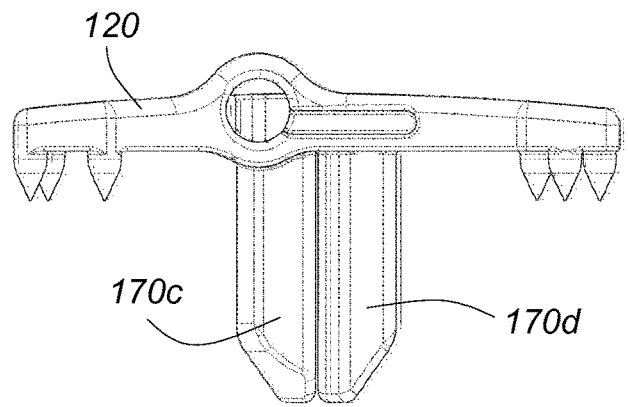
Figure 6D:
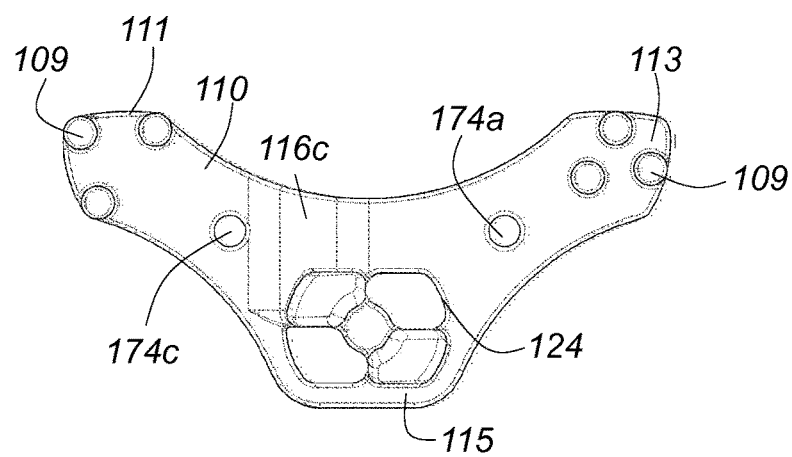
Figure 6E:
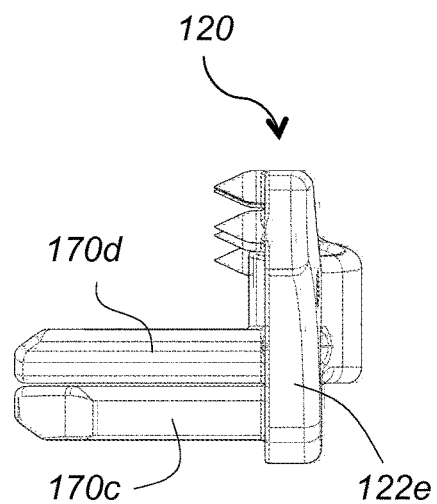

Referring to FIG. 6a-6e, spinous process fixation implant 100 includes first component 110, second component 120, and set screws 140a, 140b. First component 110 includes an elongated body 112 and two integral posts 170a, 170b. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115, as shown in FIG. 6d. Middle portion 115 includes opening 172c, 172d extending from the left surface 112c to the right surface 112d. Top portion 111 includes teeth 109 protruding from the top of right surface 112d. Bottom portion 113 also includes teeth 109 protruding from the bottom of right surface 112d. Openings 172c, 172d have rectangular cross-sections and are dimensioned to be slightly larger or equal to the dimensions of posts 170c, 170d of component 120, respectively, so that posts 170c, 170d can pass through them. Middle portion 115 also includes opening 116c extending from the front surface 112a to the back surface 112b. Opening 116c receives set screw 140a and has dimensions matching the dimensions of screw 140a. Screw 140a secures the position of post 170b onto post 170d of the second component 120 within opening 172d. Posts 170a, 170b have an essentially parallelepiped structure and are integral with component 110. Posts 170a, 170b extend perpendicularly to the right side surface 112d of the elongated body 112 from its middle portion 115. Elongated body 112 also includes cut outs 174a, 174c, 174d used for grabbing or gripping features for inserter to hold onto.

Referring to FIG. 6b, second component 120 is the same as the first component 110 and is rotated 180 degrees relative to the orientation of the first component 110. Second component 120 includes an elongated body 122 and two integral posts 170c, 170d. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Middle portion 125 includes opening 172a, 172b extending from the left surface 122c to the right surface 122d. Top portion 121 includes teeth 109 protruding from the top of left surface 122c. Bottom portion 123 also includes teeth 109 protruding from the bottom of left surface 122c. Openings 172a, 172b have rectangular cross-sections and are dimensioned to be slightly larger or equal to the dimensions of posts 170a, 170b of first component 110, respectively, so that posts 170a, 170b can pass through them. Middle portion 125 also includes opening 116d extending from the front surface 122a to the back surface 122b. Opening 116d receives set screw 140b and has dimensions matching the dimensions of screw 140b. Screw 140b secures the position of post 170c onto post 170a of the first component 110 within opening 172c. Posts 170c, 170d have an essentially parallelepiped structure and are integral with second component 120. Posts 170c, 170d extend perpendicularly to the left side surface 122c of the elongated body 122 from its middle portion 125. Elongated body 122 also includes cut outs 174b, 174e, 174f used as gripping or grabbing features for the inserter tool.

In operation first component 110 is placed in contact with the left sides of top and bottom spinous process 90a, 90b of adjacent vertebras 80a, 80b, respectively. Posts 170a, 170b are placed in the space between the top and bottom spinous processes 90a, 90b. Next, second component 120 is placed in contact with the right sides of top and bottom spinous process 90a, 90b of adjacent vertebras 80a, 80b, respectively, posts 170a, 170b of the first component 110 are inserted into openings 172a, 172b of the second component 120, and posts 170c, 170d of the second component 120 are inserted into openings 172c, 172d of the first component 110, respectively. Fully inserted posts 170a, 170b, 170c, 170*d* interface with the corresponding openings 172*a*, 172*b*, 172*c*, 172*d* and with each other to form a hub structure 124, as shown in FIG. 6*d*. Next, the two components 110, 120 are pressed against the left and right of the top and bottom spinous processes 90*a*, 90*b*, respectively and set screws 140*a*, 140*b* are screwed into openings 116*c*, 116*d*, to compress and secure the position of the two components 110, 120, respectively. Teeth 109 at the top and bottom portions of components 110, 120 penetrate into the sides of the top and bottom spinous processes 90*a*, 90*b*, respectively.

Figure 7A:
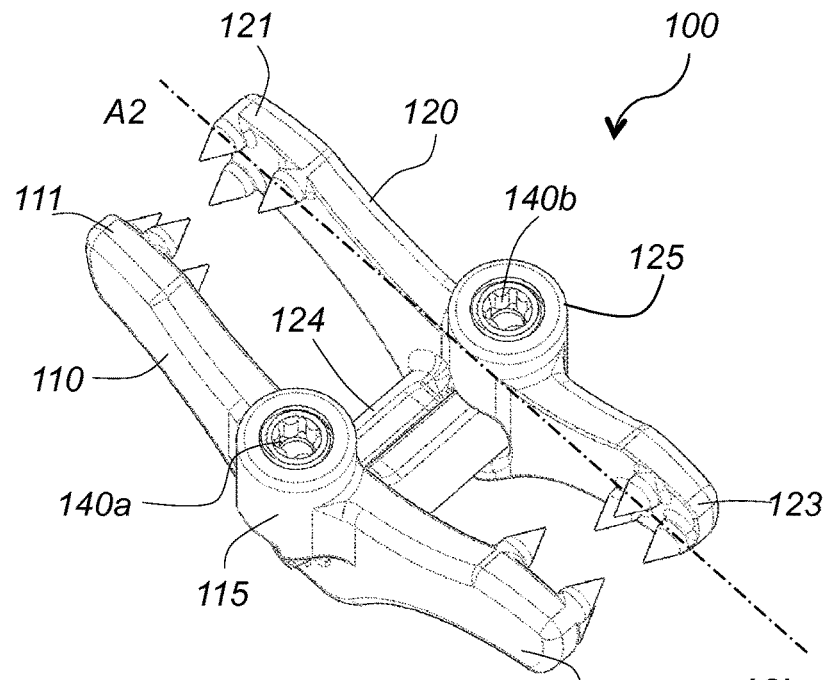
FIG. 7a is a perspective view of a sixth embodiment of the interspinous fixation implant according to this invention.

Referring to FIG. 7*a*-7*f*, spinous process fixation implant 100 includes first component 110, second component 120, and set screws 140*a*, 140*b*. First component 110 includes an elongated body 112 and one integral post 170*a*. Elongated body 112 has an essentially parallelepiped structure having parallel front and back surfaces 112*a*, 112*b*, parallel left and right side surfaces 112*c*, 112*d* and parallel top and bottom surfaces 112*e*, 112*f*, respectively. Elongated body 112 is convexly curved so that its top and bottom portions 111, 113 protrude forward relative to its middle portion 115, as shown in FIG. 7*f*. Middle portion 115 includes an opening 172*b* extending from the left surface 112*c* to the right surface 112*d*. Top portion 111 includes teeth 109 protruding from the top of right surface 112*d*. Bottom portion 113 also includes teeth 109 protruding from the bottom of right surface 112*d*. Opening 172*b* has a semi-circular cross-section and is dimensioned to be slightly larger or equal to the dimensions of post 170*b* of component 120, so that post 170*b* can pass through it. Middle portion 115 also includes a cylindrical projection 115*a* having an opening 116*c* extending from the front surface 112*a* to the back surface 112*b*.

Opening 116*c* receives set screw 140*a* and has dimensions matching the dimensions of screw 140*a*. Screw 140*a* secures the position of post 170*b* of the second component 120 onto post 170*a* of the first component 110 within opening 172*b*. Post 170*a* is integral with component 110 and has an essentially hollow semi-cylindrical structure. Post 170*a* extends perpendicularly to the right side surface 112*d* of the elongated body 112 from its middle portion 115. Post 170*a* is adjacent to opening 172*b* and is oriented so that its cross-section forms a full circle together with the semi-circular opening 172*b*, as shown in FIG. 7*f*.

Figure 7B:
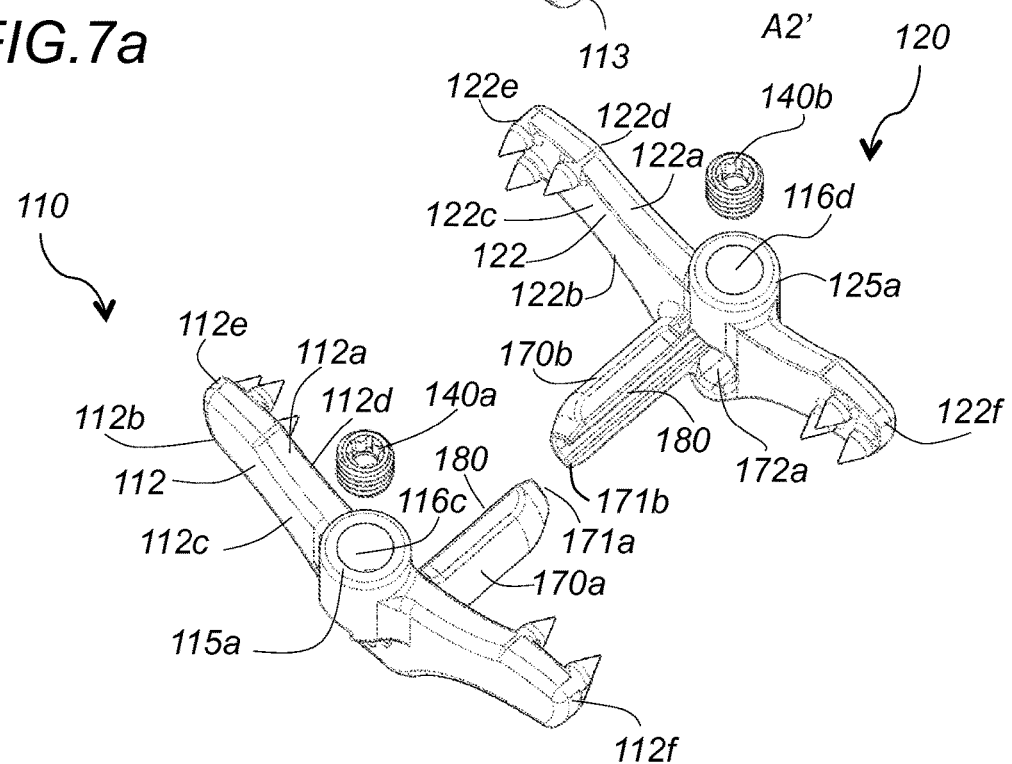

Referring to FIG. 7*b*, second component 120 is the same as the first component 110 and is rotated 180 degrees relative to the orientation of the first component 110. Second component 120 includes an elongated body 122 and one integral post 170*b*. Elongated body 122 has an essentially parallelepiped structure having parallel front and back surfaces 122*a*, 122*b*, parallel left and right side surfaces 122*c*, 122*d* and parallel top and bottom surfaces 122*e*, 122*f*, respectively. Elongated body 122 is also convexly curved so that its top and bottom portions 121, 123 protrude forward relative to its middle portion 125. Middle portion 125 includes an opening 172*a* extending from the left surface 122*c* to the right surface 122*d*. Top portion 121 includes teeth 109 protruding from the top of left surface 122*c*. Bottom portion 123 also includes teeth 109 protruding from the bottom of left surface 122*c*. Opening 172*a* has a semi-circular cross-section and is dimensioned to be slightly larger or equal to the dimensions of post 170*a* of component 110, so that post 170*a* can pass through it. Middle portion 125 also includes a cylindrical projection 125*a* having an opening 116*d* extending from the front surface 122*a* to the back surface 122*b*. Opening 116*d* receives set screw 140*b* and has dimensions matching the dimensions of screw 140*a*. Screw 140*a* secures the position of post 170*a* of the first component 110 onto post 170*b* of the second component 120 within opening 172*a*. Post 170*b* is integral with component 120 and has an essentially hollow semi-cylindrical structure. Post 170*b* extends perpendicularly to the left side surface 122*c* of the elongated body 122 from its middle portion 125. Post 170*b* is adjacent to opening 172*a* and is oriented so that its cross-section forms a full circle together with the semi-circular opening 172*a*. Posts 170*a*, 170*b* have tapered front ends 171*a*, 171*b*. Tapered front ends 171*a*, 171*b*, help the insertion of the posts 170*a*, 170*b* through the interspinous area 85 and the openings 172*a*, 172*b*, respectively.

Figure 8A:
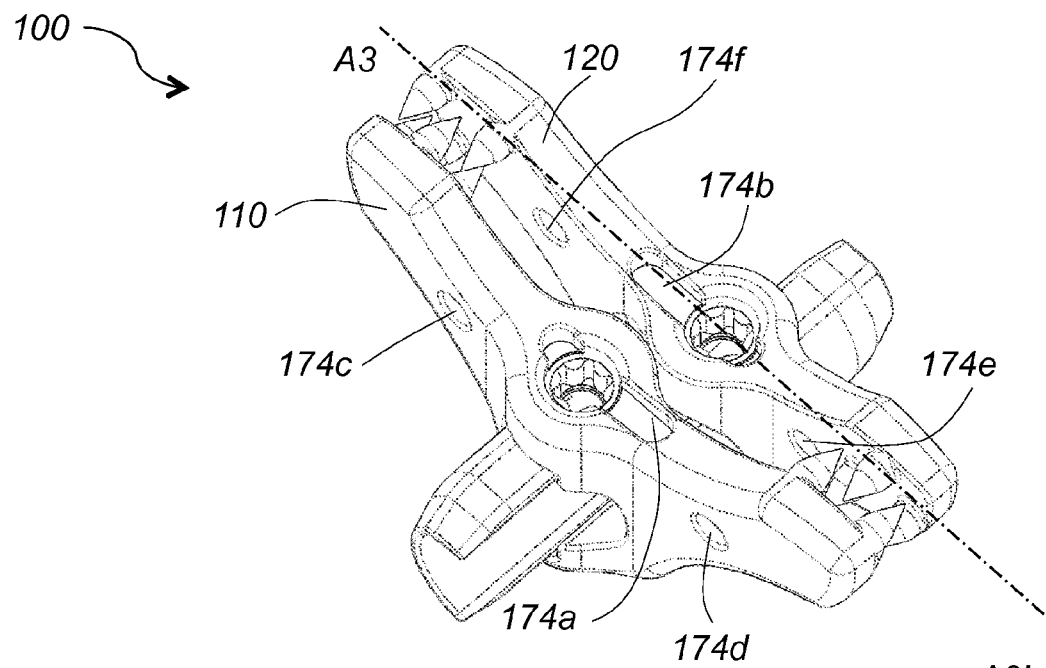
FIG. 8a is a perspective view of a seventh embodiment of the interspinous fixation implant according to this invention.
Figure 8B:
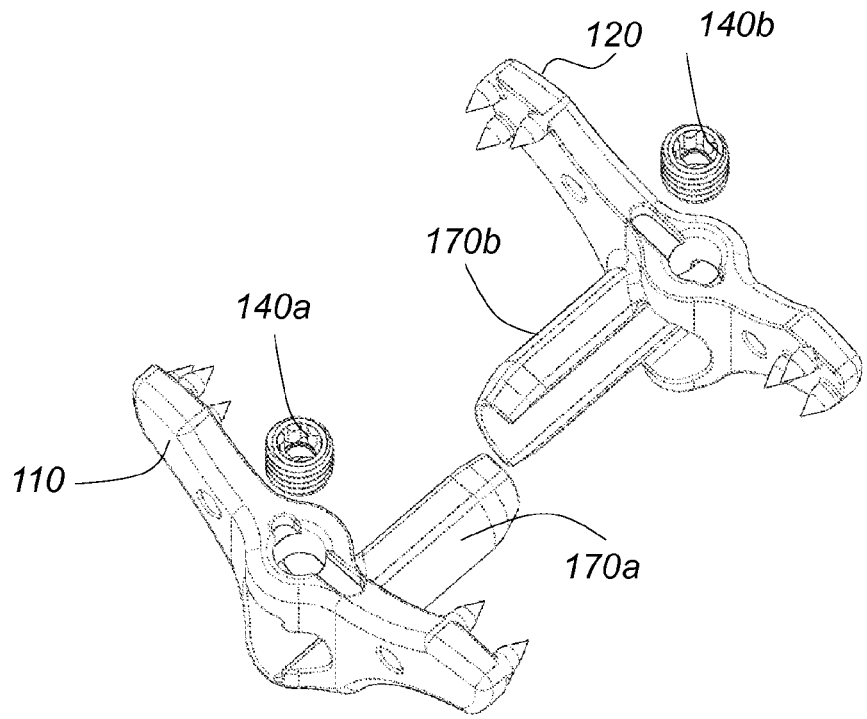
Figure 8F:
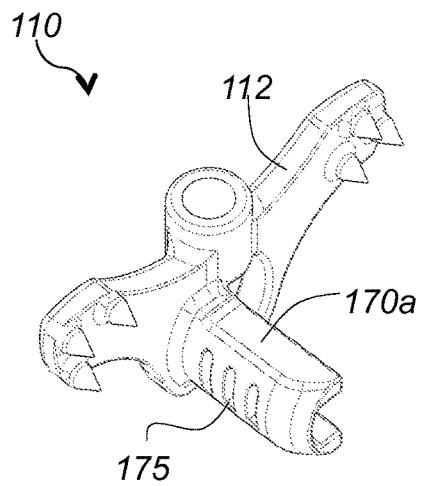
Figure 8G:
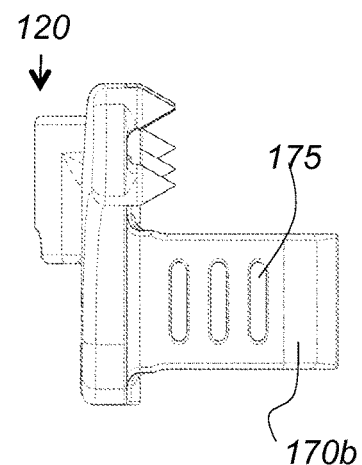

In operation first component 110 is placed in contact with the left sides of top and bottom spinous process 90*a*, 90*b* of adjacent vertebras 80*a*, 80*b*, respectively, as shown in FIG. 7*c*. Post 170*a* is placed in the space 85 between the top and bottom spinous processes 90*a*, 90*b*. Next, second component 120 is placed in contact with the right sides of top and bottom spinous process 90*a*, 90*b* of adjacent vertebras 80*a*, 80*b*, respectively. Post 170*a* of the first component 110 is inserted into opening 172*a* of the second component 120, and post 170*b* of the second component 120 is inserted into openings 172*b* of the first component 110. Fully inserted posts 170*a*, 170*b* interface with the corresponding openings 172*a*, 172*b*, and with each other to form a hollow cylindrical hub structure 124, as shown in FIG. 7*a*. Next, the two components 110, 120 are pressed against the left and right of the top and bottom spinous processes 90*a*, 90*b*, respectively and set screws 140*a*, 140*b* are screwed into openings 116*c*, 116*d*, to compress and secure the position of the two components 110, 120, respectively. Teeth 109 at the top and bottom portions of components 110, 120 penetrate into the sides of the top and bottom spinous processes 90*a*, 90*b*, respectively. Graft material 180 is usually inserted into the hollow cylindrical hub structure 124 for promoting fusion of the two spinous processes 90*a*, 90*b*. In the embodiment of FIG. 8*f* and FIG. 8*g*, posts 170*a* and 170*b* include side openings 175 that allow the graft material 180 placed in the hollow cylindrical hub structure 124 to promote cross-fusion within the interspinous ligament at 85. In the embodiment of FIG. 8*a*-8*e*, the spinous process fixation implant 100 is similar to the embodiment in FIG. 7*a* and it includes cut outs 174*a*, 174*b*, 174*c*, 174*d*, 174*e*, 174*f* used as gripping or grabbing features for the inserter tool.

Figure 9A:
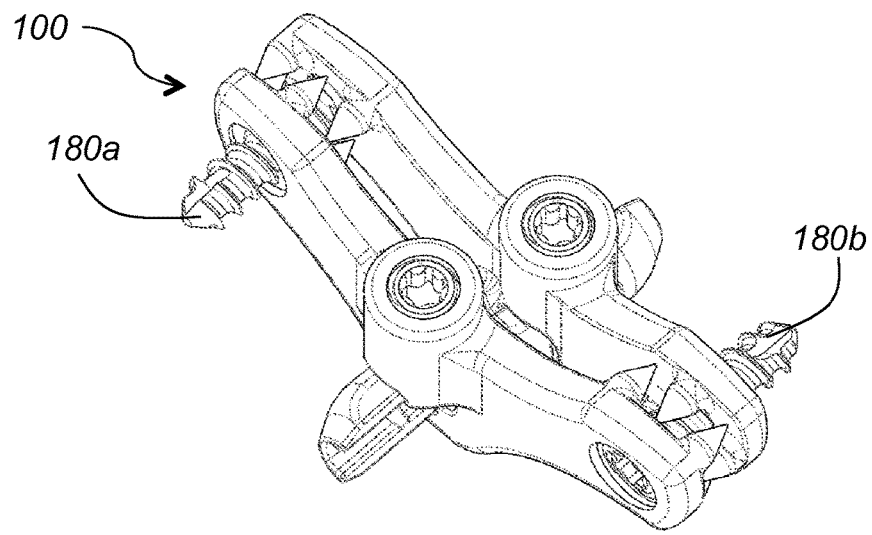
FIG. 9a is a perspective view of an eight embodiment of the interspinous fixation implant according to this invention.
Figure 9B:
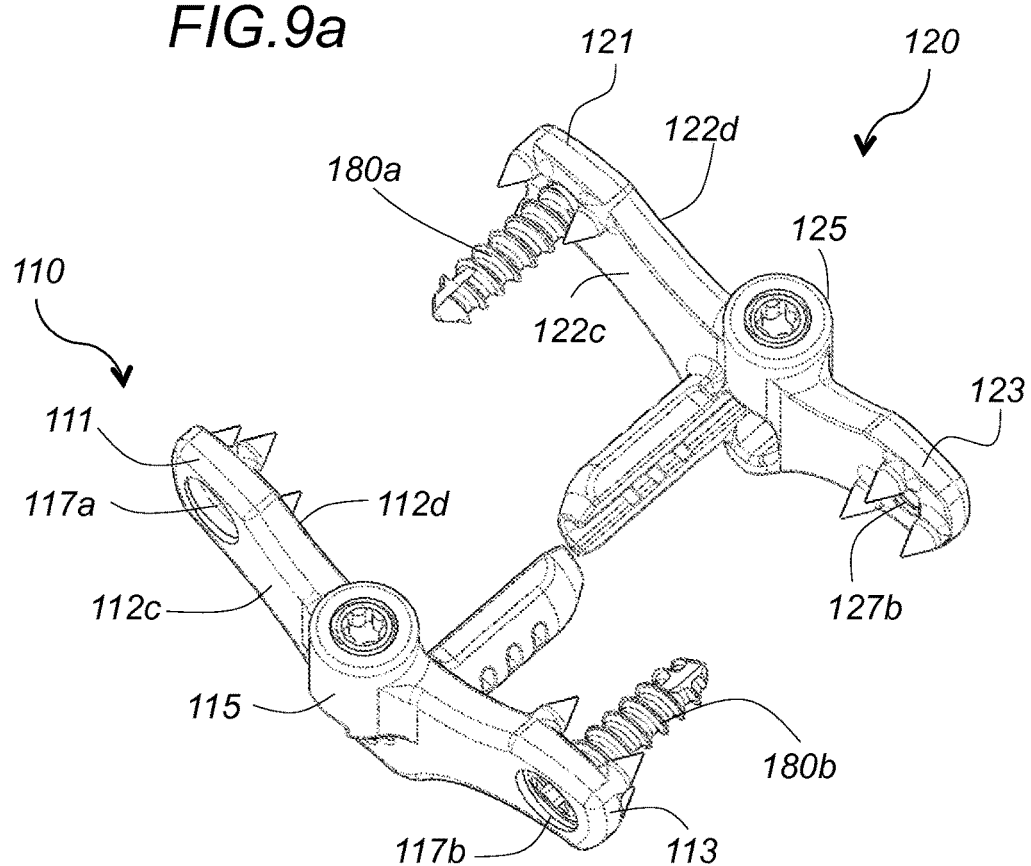
Figure 9C:
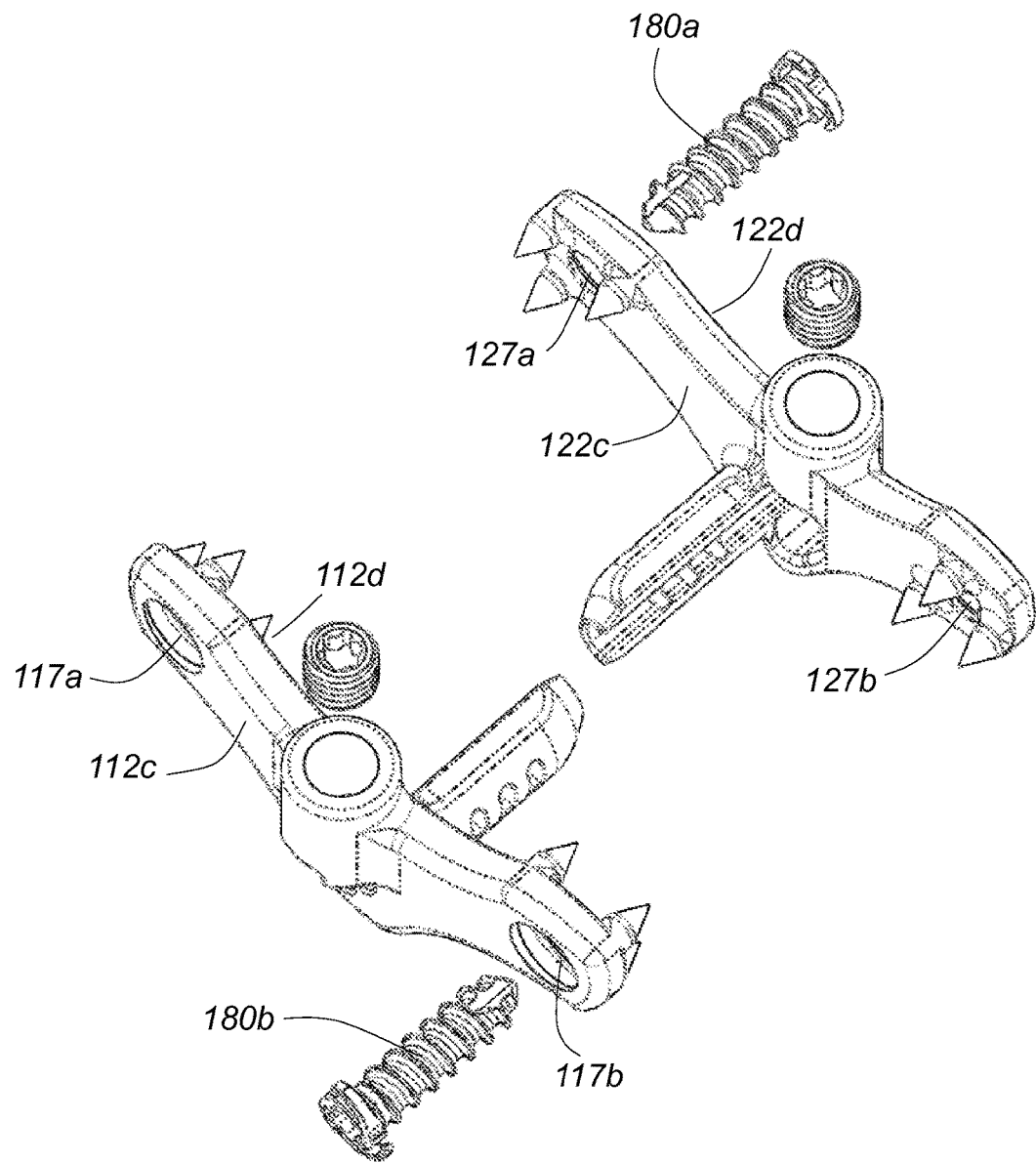

Referring to FIG. 9*a*-9*b*, the embodiment of the spinous process implant 100 is similar to the embodiments in FIG. 7*a* and FIG. 8*f* and it further includes openings 117*a*, 117*b* formed in the top and bottom portions of first component 110, respectively, and openings 127*a*, 127*b* formed in the top and bottom portions of second component 120, respectively. Openings 117*a*, 117*b* extend from the left surface 112*c* to the right surface 112*d* of component 110 and openings 127*a*, 127*b* extend from the left surface 122*c* to the right surface 122*d* of component 120. Openings 117*a*, 117*b*, 127*a*, 127*b* have threaded inner surfaces that are dimensioned to engage with the threads of top and bottom screws 180*a*, 180*b*, as shown in FIG. 9*a*. Openings 117*a*, 117*b*, 127*a*, 127*b* have an essentially circular perimeter at the top portion of the plate. The major diameter 181*a* of openings 117*a*, 117*b* near the left side surface 112*c* is larger than the minor diameter 181*b* near the right side surface 112*d*, as shown in FIG. 9*d*. Similarly, the major diameter 181*a* of openings 127*a*, 127*b* near the right side surface 122*d* is larger than the minor diameter 181*b* near the left side surface 122*c*. A lip 182 is formed around the top of each opening 117*a*, 117*b*, 127*a*. Lip 182 is designed to interface with flexible arms 184*a*-184*c* extending from the screw head 186 and thereby to lock the screw 180*a* onto the second component 120, as will be explained below.

Referring to FIG. 9e, self-tapping screw 180a has a threaded main body 185 for engaging the inner threads in openings 127a, 117a and a head 186. Main body 185 includes threads 185a. Head 186 has a flat top 187, a cylindrical center 186a and angled bottom sides 188a, 188b, as shown in FIG. 9f. Top 187 includes an opening 189 extending into the main body 185. Opening 189 has six lobes 189a-189f, and at the bottom between two adjacent lobes six grooves 199a-199f are formed. The geometry of opening 189 interfaces with the geometry of a screw engaging component at the end of a driver tool used for screwing in and/or out screw 180a. Three flexible arms 184a-184c extend tangentially from the outer side of the cylindrical center 186a and curve around the head 186. The effective diameter of the screw head 186 including the arms 184a-184c in the unflexed position is larger than the top major diameter 181a of openings 117a, 117b, 127a, 127b. Arms 184a-184c flex inward toward the central axis 190 when they come in contact with lip 182 of the openings 117a, 117b, 127a, 127b while the screw 180a is being rotated clock-wise to be driven into the spinous process and the opposite component. The effective diameter of the screw head 186 including the arms 184a-184c in the inward flexed position is smaller than the top major diameter 181a of openings 117a, 117b, 127a, 127b, and this allows the screw head 122 including the arms 184a-184c to move below the lip 182. Once the arms 184a-184c are below the lip 182 they expand back up to their unflexed position within a space 193 formed in the opening 117a between the lip 182 and the chamfered sides 196 at the bottom portion of the opening 117a, shown in FIG. 9g. Once the entire screw head 186 is in place within space 193, the lip 182 prevents the screw head from accidentally moving up (i.e., backing out) from space 193 due to stresses applied during spinal motion. In cases where the mounted screw is rotated counter-clockwise, arms 184a-184c hit the lip 182 and the sidewalls of the opening 117a and flex outward away from the central axis 190, thereby increasing the effective diameter of the screw head so that it is even larger than the top major diameter 181a. This outward flexing of the arms 184a-184c prevents the screw head 186 from accidentally moving up and out of space 193. The surgeon may pull out the screw 180a with the above mentioned driver tool.

The bottom portion of the openings 117a-117b, 127a, and 127b is oval-shaped and has two parallel straight sides and two opposite curved sides. The distance between the two parallel straight sides (width of the opening) (minor diameter) 181b is smaller than the major diameter of the threaded portion 185 of the screw 180a and equal or larger than the minor diameter of the threaded portion 185. The distance between the curved sides of the opening (major diameter) 181a is larger or equal to the major diameter of the threaded portion 185 of the screw. The oval-shaped structure of the bottom portion of openings 117a-117b, 127a, 127b cooperates with the screw threads 185 to allow the screw 180a to move downward or upwards through the opening when the screw 180a is rotated and prevents backing out or moving forward of the screw 180a when the screw is pushed up or down, respectively. Since the width 181b of the opening at the bottom portion is smaller than the major diameter of the threaded portion 185 of the screw 180a and the major diameter 181a is larger or about the same size as the major diameter of the threaded portion 185, the screw threads 185a move through the opening as they are rotated clock-wise only when they are in line with the diameter 181a. Once the screw threads 185a pass below the bottom portion of the opening, they cannot be accidentally pushed straight up because they will hit the straight parallel sides of the oval-shaped opening, whose spacing 181b is smaller than the major diameter of the screw. This "threading" of the screw 180a through the oval-shaped opening (i.e. "captive geometry") of the bottom portion of the component 110 locks the screw 180a to the component 110 and prevents accidental backing out of the screw 180a.

Figure 10A:
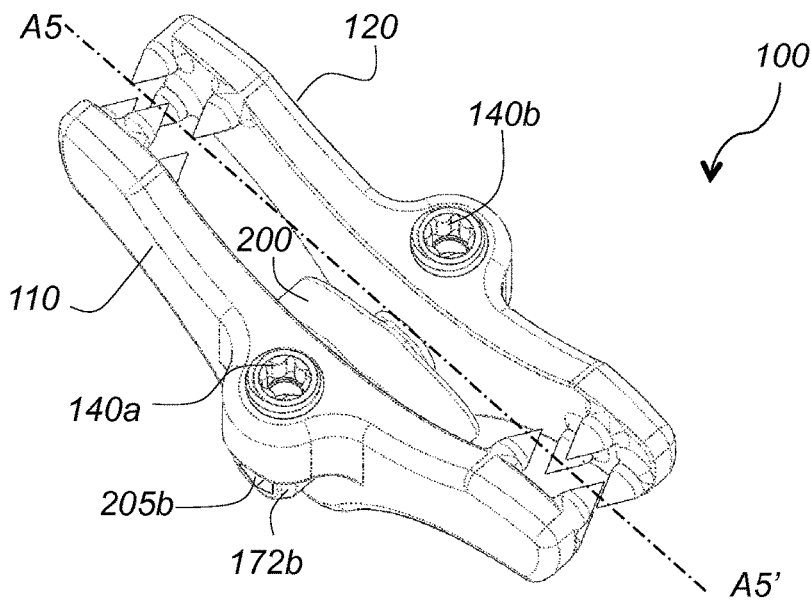
FIG. 10a is a perspective view of a ninth embodiment of the interspinous fixation implant according to this invention.
Figure 10B:
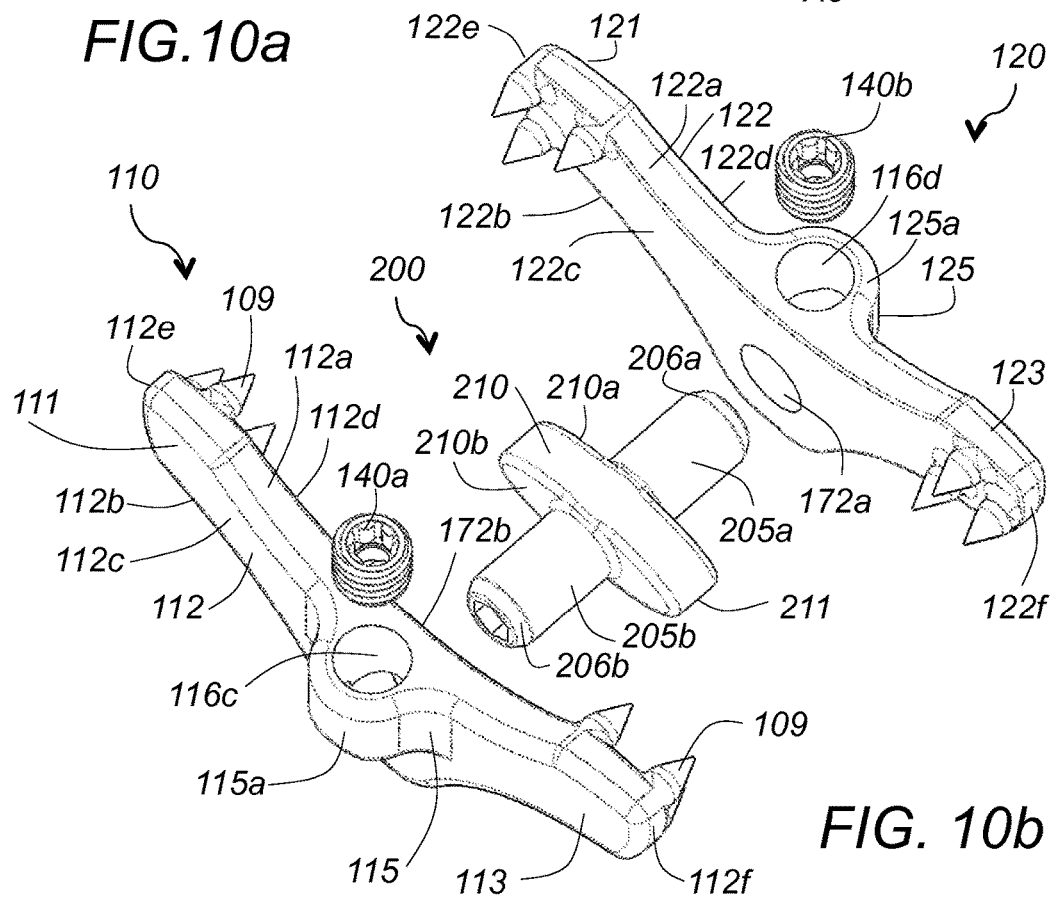
Figure 10C:
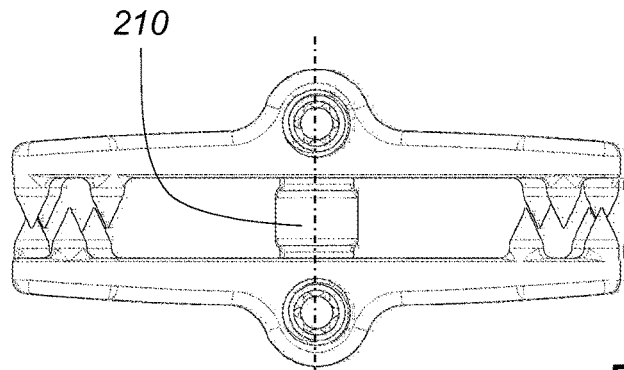
FIG. 10c is a front view of the interspinous fixation implant of FIG. 10a with the hub plate element oriented in a first direction.
Figure 10D:
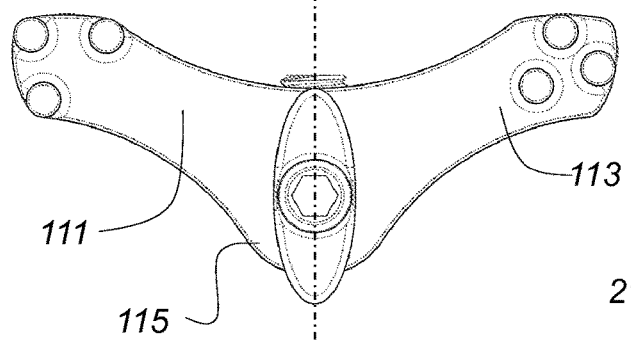
FIG. 10d is a side view of the interspinous fixation implant of FIG. 10c.

Referring to FIG. 10a-10f, spinous process fixation implant 100 includes first component 110, second component 120, hub 200 and set screws 140a, 140b. First component 110 includes an elongated body 112. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115, as shown in FIG. 10d. Middle portion 115 includes an opening 172b extending from the left surface 112c to the right surface 112d. Top portion 111 includes teeth 109 protruding from the top of right surface 112d. Bottom portion 113 also includes teeth 109 protruding from the bottom of right surface 112d. Opening 172b has a circular cross-section and is dimensioned to be slightly larger or equal to the dimensions of post 205b of hub 200, so that the post 205b can pass through it. Middle portion 115 also includes a cylindrical projection 115a having an opening 116c extending from the front surface 112a to the back surface 112b. Opening 116c receives set screw 140a and has dimensions matching the dimensions of screw 140a. Screw 140a secures the position of post 205b of hub 200 within opening 172b.

Referring to FIG. 10b, second component 120 is a mirror-image of first component 110 and includes an elongated body 122. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Middle portion 125 includes an opening 172a extending from the left surface 122c to the right surface 122d. Top portion 121 includes teeth 109 protruding from the top of right surface 122d. Bottom portion 123 also includes teeth 109 protruding from the bottom of right surface 122d. Opening 172a has a circular cross-section and is dimensioned to be slightly larger or equal to the dimensions of post 205a of hub 200, so that post 205a can pass through it. Middle portion 125 also includes a cylindrical projection 125a having an opening 116d extending from the front surface 122a to the back surface 122b. Opening 116d receives set screw 140b and has dimensions matching the dimensions of screw 140b. Screw 140b secures the position of post 205a within opening 172a.

Figure 10E:
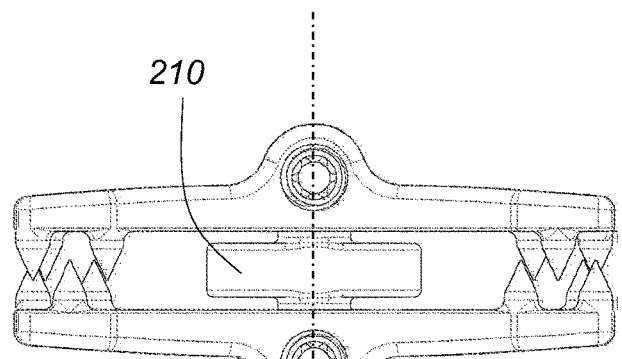
FIG. 10e is a front view of the interspinous fixation implant of FIG. 10a with the hub plate element 210 oriented in a second direction.
Figure 10F:
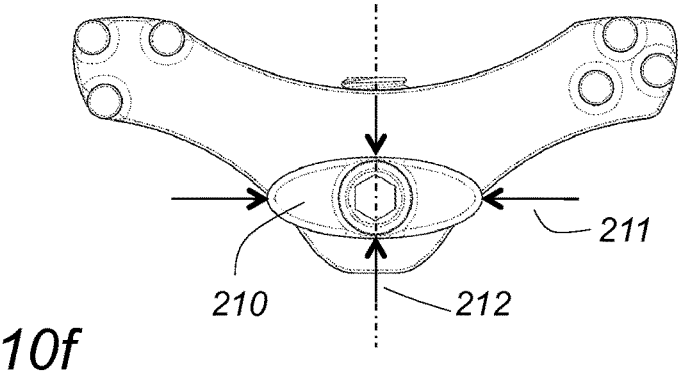
FIG. 10f is a side view of the interspinous fixation implant of FIG. 10e.

Hub 200 includes an oval shaped plate 210 that has integral posts 205a, 205b extending perpendicular to its side surfaces 210a, 210b, respectively. Oval plate 210 has a major diameter 211 and a minor diameter 212 and is rotatable around an axis passing through posts 205a, 205b. Posts 205a, 205b have tapered front ends 206a, 206b that help the insertion of the posts 205a, 205b through the interspinous area 85 and the openings 172a, 172b, respectively. When hub 200 is inserted in the interspinous area 85, oval plate 210 is oriented so that its long axis is horizontal to the spinous processes, as shown in FIG. 10c. Next, the hub 200 is rotated so that the oval plate 210 rotates from horizontal to vertical orientation (as shown in FIG. 10e) to create interspinous distraction.

Referring to FIG. 11a-11f, spinous process fixation implant 100 includes first component 110, second component 120, first and second hub components 220a, 220b, sliders 230a, 230b, locking plate 235, sliding pins 236a, 236b and set screw 140a. First component 110 includes an elongated body 112 that has an essentially parallelepiped structure having parallel front and back surfaces 112a, 112b, parallel left and right side surfaces 112c, 112d and parallel top and bottom surfaces 112e, 112f, respectively. Elongated body 112 includes an elongated slot 231 extending through the middle portion 115 along axis A6-A6' and from left surface 112c to surface 112d. Top portion 111 includes teeth 109 protruding from the top of right surface 112d. Bottom portion 113 also includes teeth 109 protruding from the bottom of right surface 112d. Slot 231 has a rectangular cross-section and is dimensioned to be slightly larger or equal to the dimensions of sliders 230a, 230b, so that sliders 230a, 230b can slides through it along the axis A6-A6'. Middle portion 115 also includes a cylindrical projection 115a having an opening 116c extending from the front surface 112a to the back surface 112b. Opening 116c receives set screw 140a and has dimensions matching the dimensions of screw 140a. Screw 140a secures the position of sliders 230a, 230b and locking plate 235 within slot 231.

Figure 11A:
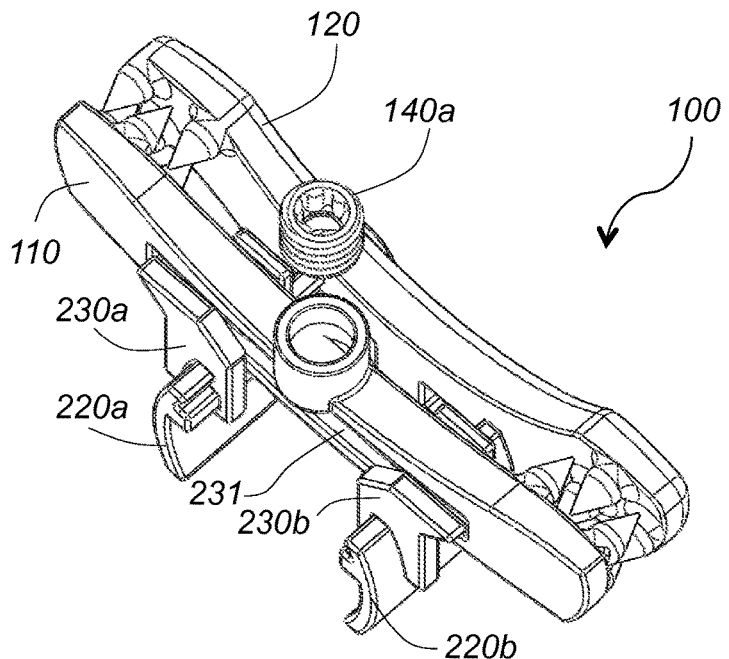
FIG. 11a is a perspective view of a tenth embodiment of the interspinous fixation implant according to this invention with the hub elements spaced apart.
Figure 11B:
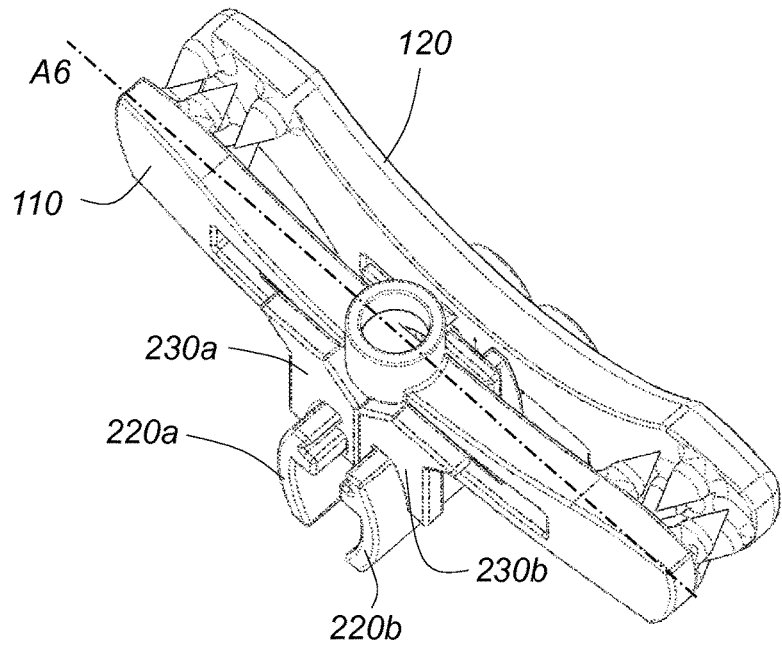
FIG. 11b is a perspective view of the interspinous fixation implant of FIG. 11a with the hub elements placed closed together.
Figure 11C:
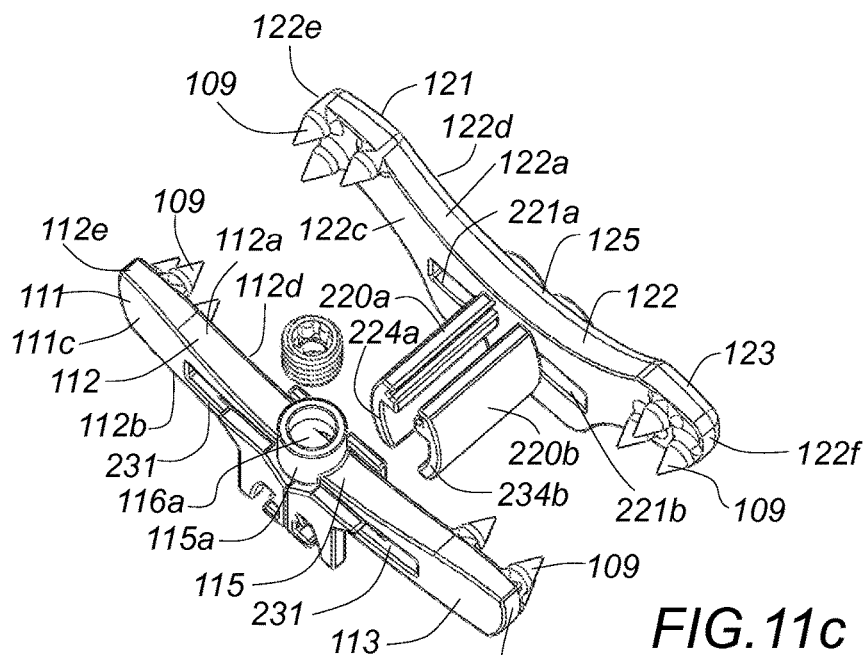
FIG. 11c is a partially exploded view of the interspinous fixation implant of FIG. 11b.
Figure 11D:
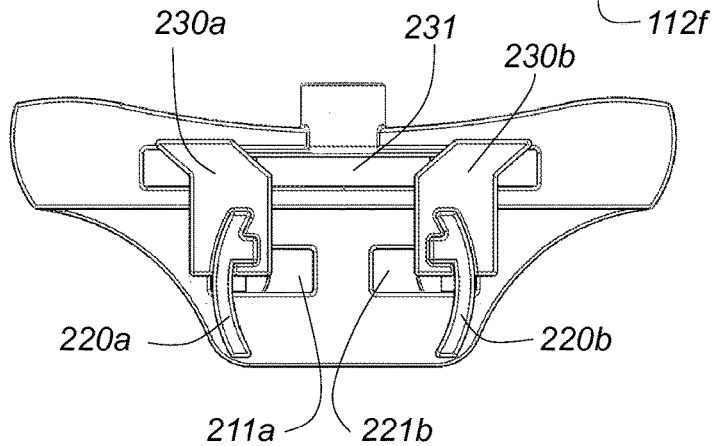
FIG. 11*d* is a side view of the interspinous fixation implant of FIG. 11*b*, with the fastening screw 140*a* untightened.
Figure 11E:
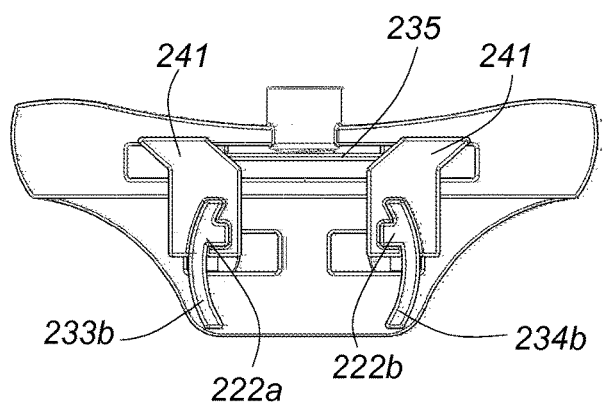
FIG. 11*e* is a side view of the interspinous fixation implant of FIG. 11*b*, with the fastening screw 140*a* tightened.

Referring to FIG. 11c, second component 120 includes an elongated body 122 that has an essentially parallelepiped structure having parallel front and back surfaces 122a, 122b, parallel left and right side surfaces 122c, 122d and parallel top and bottom surfaces 122e, 122f, respectively. Elongated body 122 includes two elongated slot 221a, 221b extending through the middle portion 125 along axis A6-A6' and from left surface 122c to surface 122d. Top portion 121 includes teeth 109 protruding from the top of right surface 122d. Bottom portion 123 also includes teeth 109 protruding from the bottom of right surface 122d.

First and second hub components 220a, 220b have an essentially hollow semi-cylindrical structure and are designed and arranged to slide within slots 221a, 221b of second component 120 with the help of sliding pins 236a, 236b, respectively, and within slot 231 of first component 110 with the help of sliders 230a, 230b, respectively. First and second hub components 220a, 220b extend perpendicularly to the left side surface 122c of the elongated body 122 from its middle portion 125. First and second hub components 220a, 220b are oriented so that their cross-sections form a full circle when they are close to each other, as shown in FIG. 11b First and second hub components 220a, 220b also include inner rectangular projections 222a, 222b, respectively, shown in FIG. 11e. End 233a of hub component 220a is placed against opening 221a of elongated component 120 and then sliding pin 236a is inserted through the slot 221a and engages the rectangular projection 222a of hub component 220a. Sliding pin 236a includes a cylindrical plate head 237a and a rectangular parallelepiped projection 238a that has a groove 239a. Groove 239a slidingly interfaces (in a tongue and groove fashion) with the rectangular projection 222a of hub component 220a and thereby locks hub component 220a within slot 221a of component 120. Projection 238a has dimensions slightly smaller than the dimensions of slot 221a and thereby sliding pin 236a and the attached hub component 220a can slide within slot 221a. Similarly, end 234a of hub component 220b is placed against opening 221b of elongated component 120 and then sliding pin 236b is inserted through the slot 221b and engages the rectangular projection 222b of hub component 220b. Sliding pin 236b includes a cylindrical plate head 237b and a rectangular parallelepiped projection 238b that has a groove 239b. Groove 239b slidingly interfaces (in a tongue and groove fashion) with the rectangular projection 222b of hub component 220b and thereby locks hub component 220b within slot 221b of component 120. Projection 238b has dimensions slightly smaller than the dimensions of slot 221b and thereby sliding pin 236b and the attached hub component 220b can slide within slot 221b.

Figure 11F:
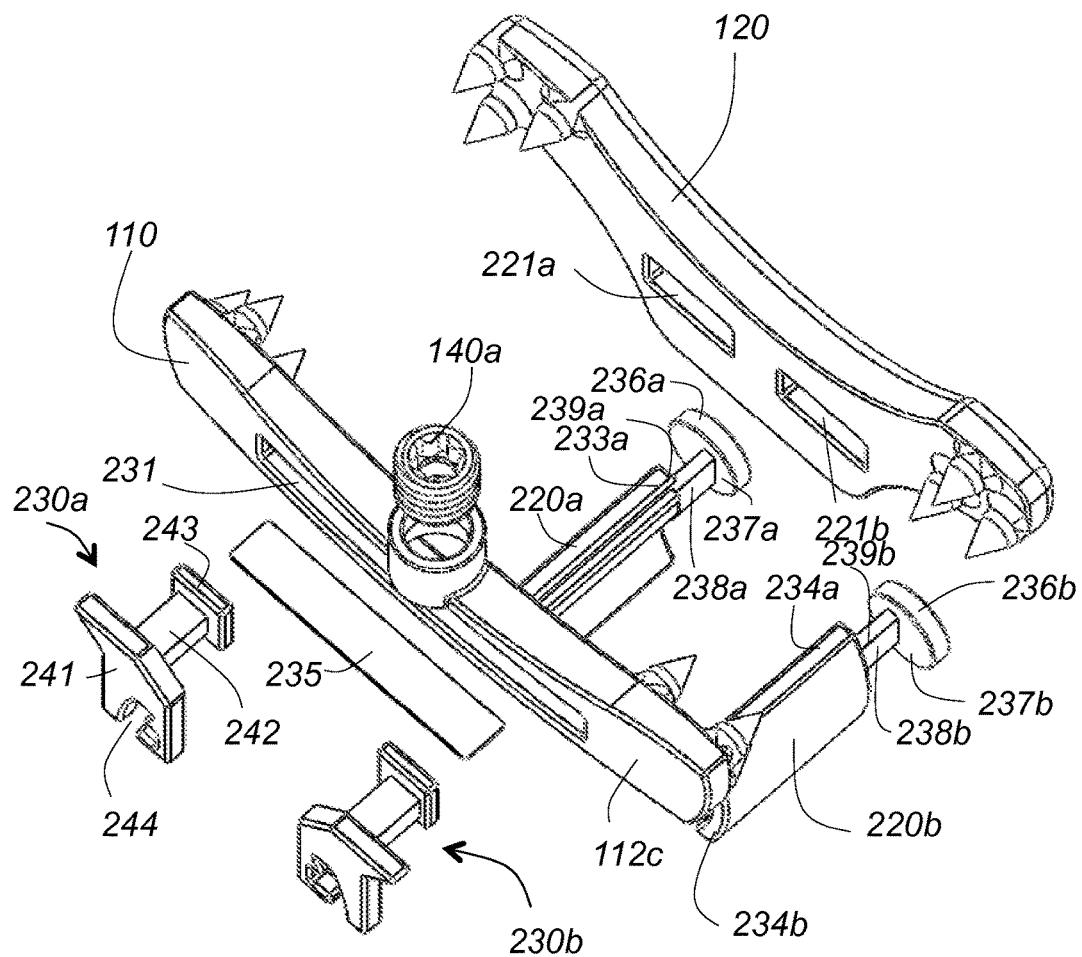
FIG. 11*f* is an exploded view of the interspinous fixation implant of FIG. 11*b*.

Referring to FIG. 11f, each slider 230a, 230b includes two parallel off-center plates 241, 243 connected with each other via a rectangular parallelepiped post 242. Plate 241 has a cut-out 244 with a cross-section matching the cross section of hub components 220a, 220b. Sliders 230a, 230b slide within slot 231 of component 110, so that rectangular parallelepiped post 242 slides within slot 231 while plate 241 is parallel and in contact with surface 112c and plate 243 is parallel and in contact with surface 112d. Ends 233b and 234b of hub components 220a, 220b engage the cut outs 244 of plates 241 of sliders 230a, 230b, respectively. This arrangement allows sliding of sliders 230a, 230b and hub components 220a, 220b within slot 231 along the direction A6-A6'. This arrangement also allows sliding of hub components 220a, 220b within cut outs 244 and thereby sliding of first component 110 along the direction perpendicular to A6-A6'. Once the desired position has been achieved locking plate 235 is inserted into slot 231 through the left side 112c and then set screw 140a is screwed down to secure the position of sliders 230a, 230b and thereby also hub components 220a, 220b within slot 231.

Referring to FIG. 12a-12d, spinous process fixation implant 100 includes first component 110, second component 120, and driving set screws 250a, 250b. First component 110 includes an elongated body 112 and one integral rib post 260. Elongated body 112 has an essentially hollow parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115. Middle portion 115 includes integral rib post 260 extending perpendicular to surface 112d. Teeth 109 protrude from the inner perimeter of surfaces 112a, 112b, 112e and 112f. Top and bottom portions 111, 113 include threaded openings 252a, 252b, respectively. Openings 252a, 252b have circular cross-section and are dimensioned to receive driving set screws 250a, 250b. The inner side 112d of component 110 is hollow and designed to hold bone graft material used for fusing the spinous processes together.

Figure 12A:
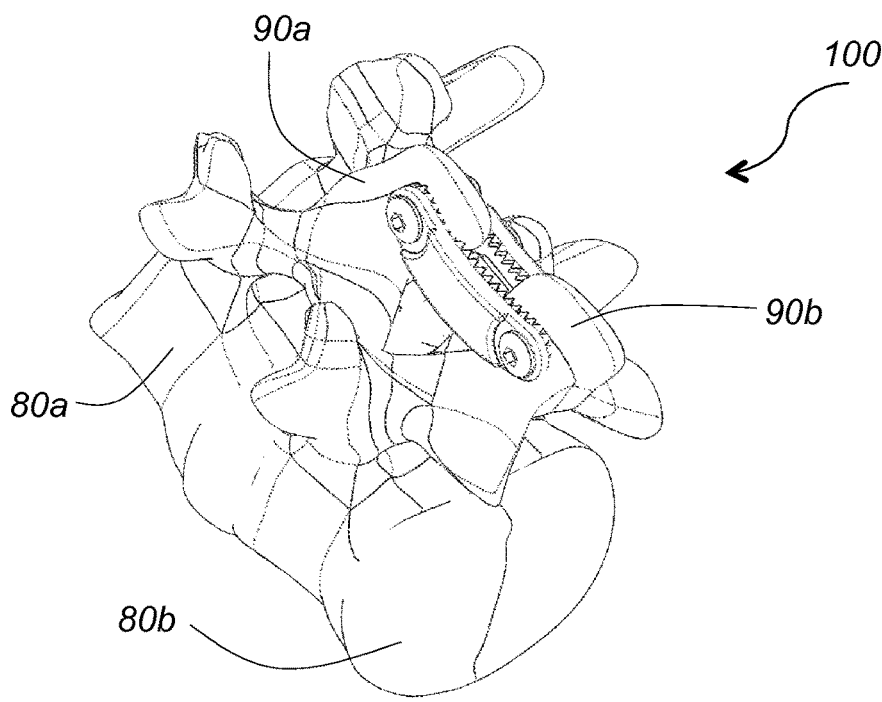
FIG. 12*a* is a perspective view of an eleventh embodiment of the interspinous fixation implant according to this invention securing two adjacent vertebras.
Figure 12B:
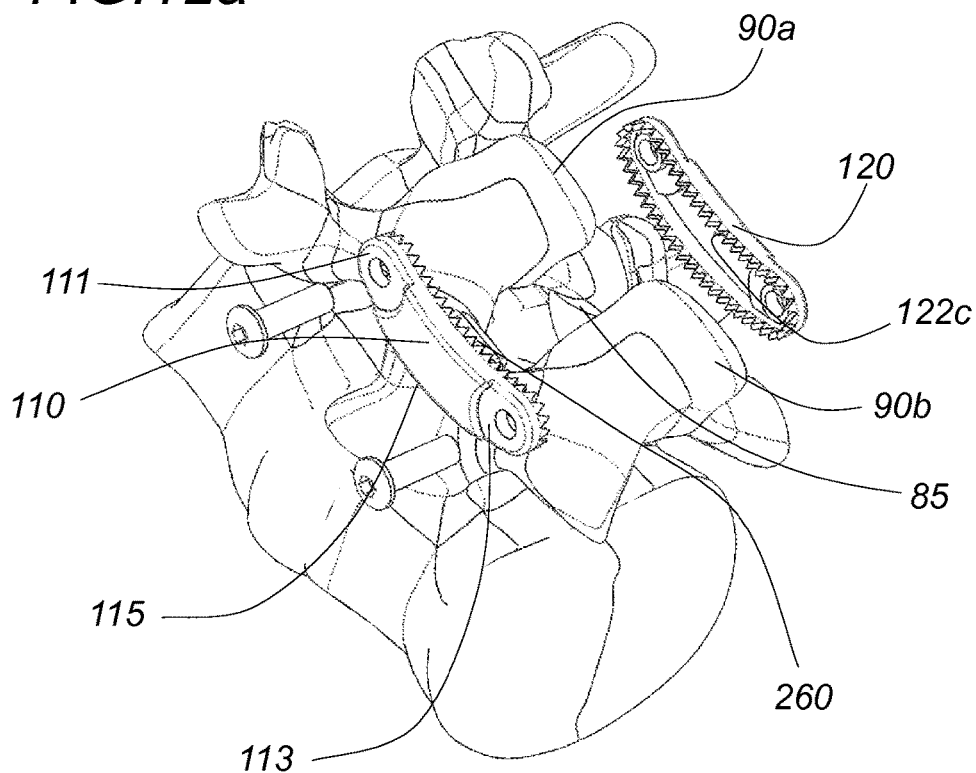
FIG. 12*b* is an exploded view of the interspinous fixation implant of FIG. 12*a*.
Figure 12C:
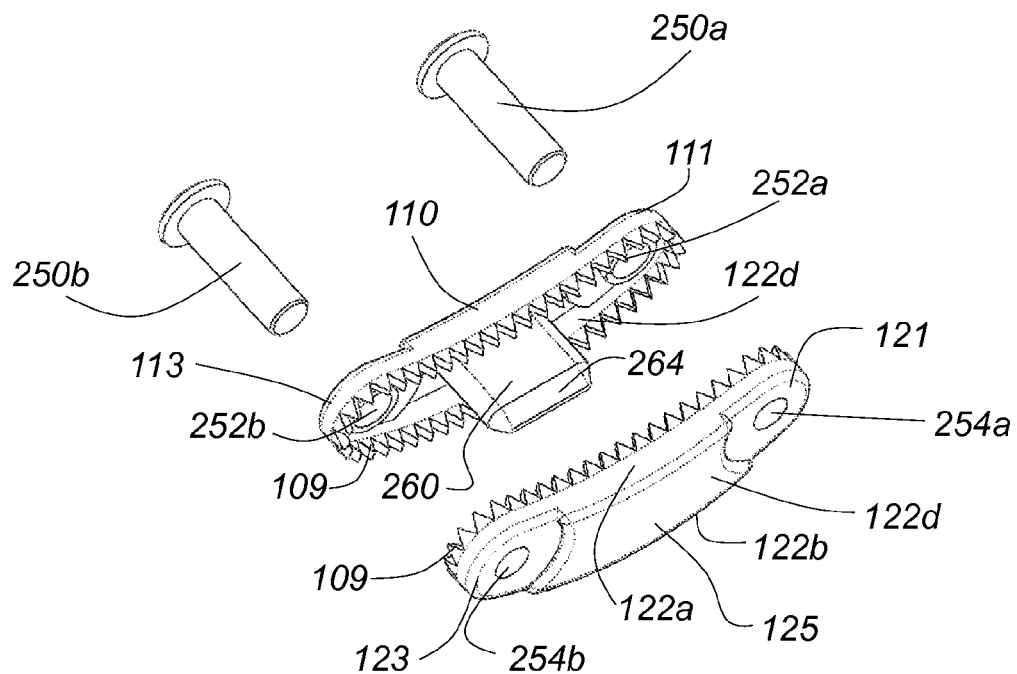
FIG. 12*c* is another exploded view of the interspinous fixation implant of FIG. 12*a*.
Figure 12D:
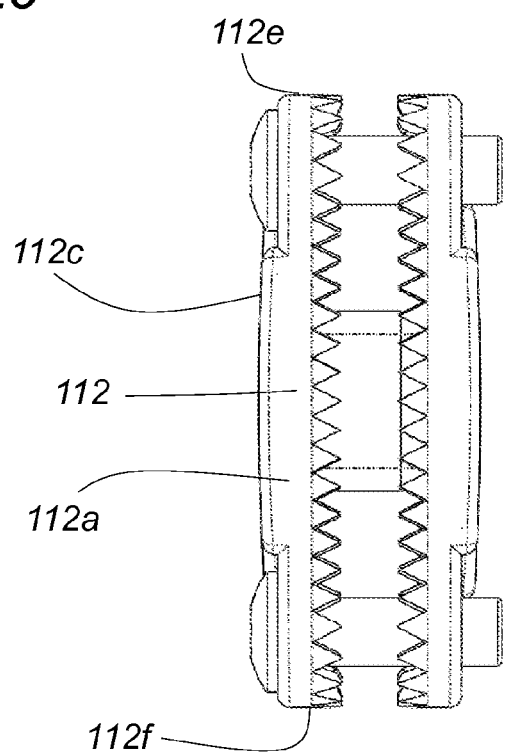
FIG. 12*d* is a front view of the interspinous fixation implant of FIG. 12*a*.

Referring to FIG. 12c, second component 120 includes an elongated body 122 that has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Teeth 109 protrude from the inner perimeter of surfaces 122a, 122b, 122e and 122f. Top and bottom portions 121, 123 include threaded openings 254a, 254b, respectively. Opening 254a, 254b have circular cross-section and are dimensioned to receive driving set screws 250a, 250b after they have passed through openings 252a, 252b and through openings formed in the upper and lower spinous processes 90a, 90b, respectively. The inner side 122d of component 120 is hollow and designed to hold bone graft material used for fusing the spinous processes together.

Figure 13A:
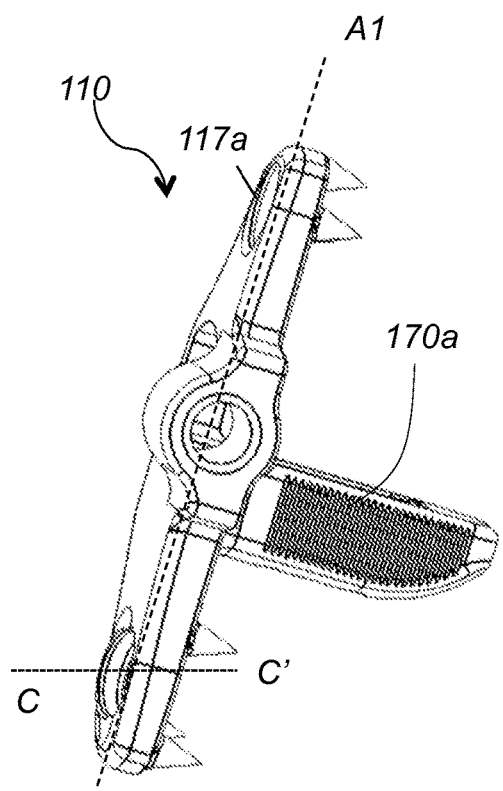
FIG. 13*a* is a front perspective view of the first component of another interspinous fixation implant.
Figure 13B:
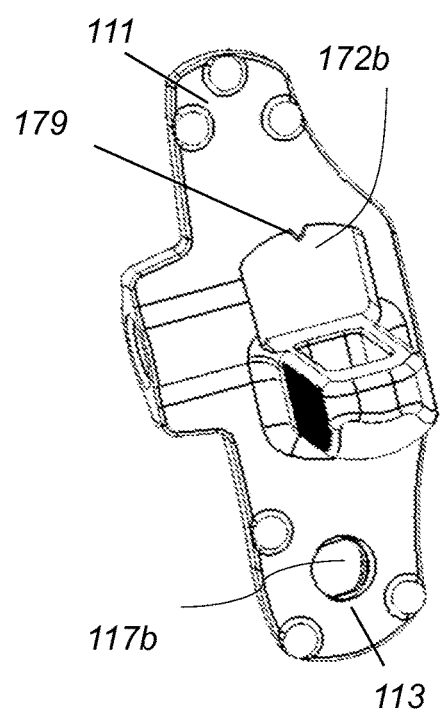
FIG. 13*b* is a right side perspective view of the first component of FIG. 13*a*.

Referring to FIG. 13a and FIG. 13b, in another embodiment of the spinous process fixation implant 100, the first component 110 includes an integral post 170a that has an essentially parallelepiped structure. Post 170a extends perpendicularly to the right side surface 112d of the elongated body 112 from its middle portion 115. Elongated body 112 also includes a rectangular opening 172b that is shaped and dimensioned to receive an essentially parallelepiped post 170b of the opposite second component 120 (not shown). Opening 172b includes a V-notch 179 that is configured to interface with a V-groove formed in post 170b of component 120. Elongated body 112 also includes a through opening 117b formed in the bottom portion 113 and a non-through opening 117a formed in the top portion 111. Through-opening 117b receives a threaded screw (not shown) that attaches the component to a spinous process. Non-through opening 117a receives a post from another elongated component that is stacked above the first component 100. This stacking configuration is used for securing a third spinous process located above or below spinous processes 90a, 90b. In this embodiment, axis C-C' of through opening 117b is not perpendicular to the elongated body axis A1-A1', thereby allowing a screw to be placed and an angle, other than 90 degrees, relative to axis A1-A1'. The arrangement of the teeth in the top portion 111 is different from the arrangement of the teeth in the bottom portion 113.

Several embodiments of the present invention have been described. Nevertheless, it will be understood that various modifications may be made without departing from the spirit and scope of the invention. Accordingly, other embodiments are within the scope of the following claims.

What is claimed is:

1. An implantable assembly for stabilization of two adjacent spinous processes in a spinal column, comprising:
   an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening;
   an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening;
   wherein said first and second components are arranged opposite and parallel to each other;
   wherein said first integral post is shaped and dimensioned to be inserted and fit within said first through-opening of the second elongated body and wherein said second integral post is shaped and dimensioned to be inserted and fit within said first through-opening of the first elongated body; and
   wherein said first and second integral posts extend from a middle portion of the first and second elongated bodies, respectively, and each of said first and second posts comprises a hollow body; and
   wherein said first through-opening of the first elongated body extends from a left surface to a right surface and comprises a first cross section, and wherein said first cross-section complements the cross-section of the first integral post and matches the cross-section of the second integral post.

2. The assembly of claim 1, wherein said first and second integral posts interface with each and form a hub spacer.

3. The assembly of claim 2, wherein each of said first and second elongated bodies comprises a parallelepiped structure having parallel front and back surfaces, parallel left and right surfaces, and parallel top and bottom surfaces, and wherein the back surfaces of said first and second elongated bodies are convexly curved so that the middle portion of each of said first and second elongated bodies protrudes relative to the top and bottom portions of each of said first and second elongated bodies, respectively.

4. The assembly of claim 1, wherein said first through-opening of the second elongated body extends from the left surface to the right surface and comprises a second cross section, and wherein said second cross-section complements the cross-section of the second integral post and matches the cross-section of the first integral post.

5. The assembly of claim 1, wherein said first and second components comprise equal dimensions and shape.

6. An implantable assembly for stabilization of two adjacent spinous processes in a spinal column, comprising:
   an elongated first component extending along a first axis and comprising a first elongated body and wherein said first elongated body comprises a first integral post, and a first through-opening, and wherein said first integral post extends from and is perpendicular to a left surface of the first elongated body and is located adjacent to said first through-opening;
   an elongated second component extending along a second axis and comprising a second elongated body and wherein said second elongated body comprises a second integral post, and a first through-opening, and wherein said second integral post extends from and is perpendicular to a right surface of the second elongated body and is located adjacent to said first through-opening;
   wherein said first and second components are arranged opposite and parallel to each other;
   wherein said first integral post is shaped and dimensioned to be inserted and fit within said first through-opening of the second elongated body and wherein said second integral post is shaped and dimensioned to be inserted and fit within said first through-opening of the first elongated body; and
   wherein each of said first and second elongated bodies further comprises a cylindrical projection extending from a middle portion perpendicular to a front surface and wherein said front surface is perpendicular to said left and right surfaces of the first and second elongated bodies, respectively, and wherein said cylindrical projection comprises a second through-opening extending from the front to a back surface of each of said first and second elongated bodies, and wherein said second through-opening intersects said first through-opening perpendicularly.

7. The assembly of claim 6, further comprising first and second set-screws dimensioned to fit within second through-openings of said first and second elongated bodies, respectively, and to secure said second and first integral posts within said first through-openings in said first and second elongated bodies, respectively.

8. The assembly of claim 6, wherein said first and second elongated bodies further comprise first and second cutouts intersecting second through-openings of said first and second elongated bodies, respectively, and wherein said cutouts are dimensioned to receive an inserter tool.

9. An implantable assembly for stabilization of two adjacent spinous processes in a spinal column, comprising:

an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening;

an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening;

wherein said first and second components are arranged opposite and parallel to each other; and wherein said first integral post is shaped and dimensioned to be inserted and fit within said first through-opening of the second elongated body and wherein said second integral post is shaped and dimensioned to be inserted and fit within said first through-opening of the first elongated body; and wherein top portions of said first and second elongated bodies comprises one or more teeth protruding from a top right surface of said first elongated body and a top left surface of said second elongated body, respectively, and wherein bottom portions of said first and second elongated bodies comprises one or more teeth protruding from a bottom right surface of said first elongated body and a bottom left surface of said second elongated body, respectively;

wherein said first through-opening of the first elongated body extends from a left surface to a right surface and comprises a first cross section, and wherein said first cross-section complements the cross-section of the first integral post and matches the cross-section of the second integral post.

10. The assembly of claim 9, wherein said first and second integral posts comprise rectangular cross-sections and are dimensioned to fit within said first through-openings in said second and first elongated bodies, respectively, and are oriented so as to interface with each other and to form a hollow parallelepiped hub spacer.

11. An implantable assembly for stabilization of two adjacent spinous processes in a spinal column, comprising:
an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening, and wherein said first through-opening of the first component is non-concentric with said first integral post;

an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening, and wherein said first through-opening of the second component is non-concentric with said second integral post;

wherein said first and second components are arranged opposite and parallel to each other; and wherein said first integral post is shaped and dimensioned to be inserted and fit within said first through-opening of the second elongated body and wherein said second integral post is shaped and dimensioned to be inserted and fit within said first through-opening of the first elongated body; and wherein said first and second integral posts comprise semi-circular cross-sections and are dimensioned to fit within said first through-openings in said second and first elongated bodies, respectively, and are oriented so as to interface with each other and to form a hollow cylindrical hub spacer.

12. The assembly of claim 11, further comprising graft material placed within said hollow hub spacer.

13. An implantable assembly for stabilization of two adjacent spinous processes in a spinal column, comprising:
an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening;

an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening;

wherein said first and second components are arranged opposite and parallel to each other;

wherein said first integral post is shaped and dimensioned to be inserted and fit within said first through-opening of the second elongated body and wherein said second integral post is shaped and dimensioned to be inserted and fit within said first through-opening of the first elongated body; and wherein said first through-opening of the first elongated body extends from a left surface to a right surface and comprises a first cross section, and wherein said first cross-section complements the cross-section of the first integral post and matches the cross-section of the second integral post; and wherein said first and second integral posts comprise one of tapered front ends or chamfered front ends.

14. An implantable assembly for stabilization of two adjacent spinous processes in a spinal column, comprising:
an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening;

an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening;

wherein said first and second components are arranged opposite and parallel to each other; and wherein said first integral post is shaped and dimensioned to be inserted and fit within said first through-opening of the second elongated body and wherein said second integral post is shaped and dimensioned to be inserted and fit within said first through-opening of the first elongated body; and wherein said first through-opening of the first elongated body extends from a left surface to a right surface and comprises a first cross section, and wherein said first cross-section complements the cross-section of the first integral post and matches the cross-section of the second integral post; and wherein said first and second integral posts comprise side openings.

15. An implantable assembly for stabilization of two adjacent spinous processes in a spinal column, comprising:

an elongated first component extending along a first axis and comprising a first elongated body and wherein said first elongated body comprises a first integral post, and a first through-opening, and wherein said first integral post extends from and is perpendicular to the first elongated body and is located adjacent to said first through-opening;

an elongated second component extending along a second axis and comprising a second elongated body and wherein said second elongated body comprises a second integral post, and a first through-opening, and wherein said second integral post extends from and is perpendicular to the second elongated body and is located adjacent to said first through-opening;

wherein said first and second components are arranged opposite and parallel to each other;

wherein said first integral post is shaped and dimensioned to be inserted and fit within said first through-opening of the second elongated body and wherein said second integral post is shaped and dimensioned to be inserted and fit within said first through-opening of the first elongated body; and wherein said first through-opening of the first elongated body extends from a left surface to a right surface and comprises a first cross section, and wherein said first cross-section complements the cross-section of the first integral post and matches the cross-section of the second integral post; and wherein said first elongated body further comprises top and bottom through-openings formed in the top and bottom portions of the first elongated body, respectively, and wherein said top and bottom through-openings extend from left to right surfaces of the first elongated body.

16. The assembly of claim 15, wherein said second elongated body further comprises top and bottom through-openings formed in the top and bottom portions of the second elongated body, respectively, and wherein said top and bottom through-openings extend from left to right surfaces of the second elongated body.

17. The assembly of claim 16, further comprising first and second locking screws dimensioned to fit within and engage threads in said top and bottom through-openings, respectively.

18. The assembly of claim 17, wherein each of said top and bottom through-openings of said first and second elongated bodies comprises a first diameter at the left surface of the first elongated body and at the right surface of the second elongated body, respectively, a second diameter at the right surface of the first elongated body and at the left surface of the second elongated body, respectively, and a third diameter in the area between the left and right surfaces of the corresponding elongated bodies and wherein said first diameter is smaller than said third diameter, thereby forming a lip at the top of said through-openings and wherein said third diameter is larger than the second diameter and said first diameter is larger than the second diameter, thereby forming a groove within the perimeter of the inner wall of said through-openings; and wherein each of said first and second locking screws comprises a threaded main body and a head and wherein said threaded main body comprises threads and wherein said head comprises one or more flexible structures configured to be flexed and inserted into said groove and then unflex and remain captured within said groove.

19. The assembly of claim 18, wherein each of said top and bottom through-openings comprises an oval-shaped perimeter and wherein said oval-shaped perimeter comprises two parallel straight sides and two opposite curved sides and wherein the distance between the two parallel straight sides is smaller than the major diameter of the threads of the first and second locking screws and wherein the distance between the curved sides is equal to or larger than the major diameter of the threads of the first and second locking screws.

20. The assembly of claim 19, wherein said head of each of said first and second locking screws comprises a cylindrical main body and wherein said one or more flexible structures comprise one or more flexible arms extending tangentially from the outer side surface of said cylindrical main body and curving counter-clockwise around the cylindrical main body and wherein the diameter of the head including the flexible arms in the unflexed position is larger than the first diameter of each of said third and fourth through openings and wherein said flexible arms are configured to flex inward toward the outer side surface of the cylindrical main body when they come in contact with said lip while the locking screw is rotated clock-wise to be driven into the spinous processes and then said flexible arms unflex once they are below the lip.

21. The assembly of claim 20, wherein said head of each of said first and second locking screws comprises an opening extending into said threaded main body and wherein said opening comprises an inner surface having six inward protruding lobes and a bottom having six grooves.

22. The assembly of claim 15, further comprising means for clamping and securing first and second spinous processes of first and second adjacent vertebras, respectively between the first and second components, and wherein said means for clamping and securing first and second spinous processes of first and second adjacent vertebras, respectively, between the first and second components, comprises at least one of teeth or first and second locking screws.

23. A method for stabilizing two adjacent spinous processes in a spinal column, comprising:

providing an implantable stabilization assembly comprising an elongated first component extending along a first axis, an elongated second component extending along a second axis and wherein said first elongated component comprises a first elongated body and wherein said first elongated body comprises a first integral post, and a first through-opening, and wherein said first integral post extends from and is perpendicular to the first elongated body and is located adjacent to said first through-opening, and wherein said second elongated component comprises a second elongated body and wherein said second elongated body comprises a second integral post, and a first through-opening, and wherein said second integral post extends from and is perpendicular to the second elongated body and is located adjacent to said first through-opening;

arranging said first and second elongated components opposite and parallel to each other and in contact with first and second spinous process of adjacent first and second vertebras, respectively;

wherein said first integral post is shaped and dimensioned to be inserted and fit within said first through-opening of the second elongated body and wherein said second integral post is shaped and dimensioned to be inserted and fit within said first through-opening of the first elongated body; and wherein said first and second integral posts extend from the middle portion of the first and second elongated bodies, respectively, and each of said first and second posts comprises a hollow body; and wherein said first through-opening of the first elongated body extends from a left surface to a right surface and comprises a first cross section, and wherein said first cross-section complements the cross-section of the first integral post and matches the cross-section of the second integral post.

24. The method of claim 23, wherein said first and second integral posts interface with each and form a hub spacer.

* * * * *